United States Patent
Foxman et al.

(10) Patent No.: US 11,965,218 B2
(45) Date of Patent: Apr. 23, 2024

(54) METHODS FOR DETECTING RESPIRATORY VIRAL INFECTION

(71) Applicant: Yale University, New Haven, CT (US)

(72) Inventors: Ellen Foxman, West Hartford, CT (US); Marie Landry, Guilford, CT (US)

(73) Assignee: YALE UNIVERSITY, New Haven, CT (US)

( * ) Notice: Subject to any disclaimer, the term of this patent is extended or adjusted under 35 U.S.C. 154(b) by 1393 days.

(21) Appl. No.: 16/340,328

(22) PCT Filed: Oct. 11, 2017

(86) PCT No.: PCT/US2017/056076
§ 371 (c)(1),
(2) Date: Apr. 8, 2019

(87) PCT Pub. No.: WO2018/071498
PCT Pub. Date: Apr. 19, 2018

(65) Prior Publication Data
US 2023/0203602 A1     Jun. 29, 2023

Related U.S. Application Data

(60) Provisional application No. 62/420,650, filed on Nov. 11, 2016, provisional application No. 62/411,101, filed on Oct. 21, 2016, provisional application No. 62/406,666, filed on Oct. 11, 2016.

(51) Int. Cl.
*C12Q 1/70* (2006.01)
*G01N 33/569* (2006.01)

(52) U.S. Cl.
CPC .......... *C12Q 1/70* (2013.01); *G01N 33/56983* (2013.01); *C12Q 2600/158* (2013.01); *G01N 2333/7158* (2013.01)

(58) Field of Classification Search
CPC ................ C12Q 1/70; C12Q 2600/158; G01N 33/56983; G01N 2333/7158
See application file for complete search history.

(56) References Cited

U.S. PATENT DOCUMENTS

2014/0128286 A1   5/2014   Khabar et al.
2016/0084762 A1   3/2016   Goix et al.

FOREIGN PATENT DOCUMENTS

WO   2009024834 A2   2/2009
WO   2012169887 A2   12/2012

OTHER PUBLICATIONS

Fensteri et al (Journal of Interferon & Cytokine , published 2011, vol. 31, No. 1, pp. 71-78).*
Imaizumi et al. (Neuroscience Research, published on 2014, vol. 84, pp. 34-42).*
Scagnolari et al. (Experimental Biology and Medicine. vol. 232, Issue 10, published by Nov. 2007, pp. 1355-1359).*
Aithal et al. (Brain Tumor Res Treat, published in.Apr. 2015; 3(1): 24-29).*
Extended European Search Report dated Jul. 3, 2020 issued for European Patent Application No. 17859661.5.
International Search Report and Written Opinion dated Feb. 20, 2018 for PCT International Application No. PCT/US2017/056076.
Partial European Search Report for European Patent Application No. 17859661.5 dated Apr. 1, 2020.
Arvia , et al., "Detection of 12 respiratory viruses by duplex real time PCR assays in respiratory samples", Mol Cell Probes. 29(6), Dec. 2015, 408-413.
Chen , et al., "Rhinovirus Induces Airway Epithelial Gene Expression Through Double-Stranded RNA and IFN-dependent Pathways", Am J Respir Cell Mol Biol. 34(2), Feb. 2006, 192-203.
Ioannidis , et al., "Plasticity and Virus Specificity of the Airway Epithelial Cell Immune Response During Respiratory Virus Infection", J Virol. 86 (10), May 2012, 5422-5436.
Landry , et al., "Antiviral Response in the Nasopharynx Identifies Patients With Respiratory Virus Infection", J Infect Dis. 217(6), Mar. 2018, 897-905.
Scagnolari , et al., "Evaluation of Viral Load in Infants Hospitalized With Bronchiolitis Caused by Respiratory Syncytial Virus", Med Microbiol Immunol. 201(3), Aug. 2012, 311-317.
Selvaggi , et al., "Interferon Lambda 1-3 Expression in Infants Hospitalized for RSV or HRV Associated Bronchiolitis", J Infect. 68(5), May 2014, 467-477.
Wagener , et al., "dsRNA-induced Changes in Gene Expression Profiles of Primary Nasal and Bronchial Epithelial Cells From Patients With Asthma, Rhinitis and Controls", Respir Res. 15(1), Jan. 2014, 9.

* cited by examiner

*Primary Examiner* — Bao Q Li
(74) *Attorney, Agent, or Firm* — Saul Ewing LLP; Kathryn Doyle; Justin Crotty

(57) ABSTRACT

The present disclosure concerns methods of detecting viral respiratory infections by analyzing biomarkers in a viral transport medium sample. In various embodiments the biomarkers are assessed by measuring mRNA or protein. In certain embodiments the biomarkers are nasal-virus induced molecules.

12 Claims, 11 Drawing Sheets

Specification includes a Sequence Listing.

CXCL11 AUC=0.905 (95% CI:0.859-0.951)
CXCL10 AUC=0.878 (95% CI: 0.826-0.930)

METHODS FOR DETECTING RESPIRATORY VIRAL INFECTION

CROSS REFERENCE TO RELATED APPLICATIONS

The present application is a 35 U.S.C. § 371 national phase application from, and claims priority to, International Application No. PCT/US2017/056076, filed Oct. 11, 2017, and published under PCT Article 21(2) in English, which claims priority under 35 U.S.C. § 119(e) to U.S. Provisional Application No. 62/406,666, filed Oct. 11, 2016, U.S. Provisional Patent Application No. 62/411,101, filed Oct. 21, 2016 and U.S. Provisional Patent Application No. 62/420,650, filed Nov. 11, 2016, each of which is incorporated herein by reference in its entirety.

STATEMENT REGARDING FEDERALLY SPONSORED RESEARCH OR DEVELOPMENT

This invention was made with government support under AI119139 awarded by National Institutes of Health. The government has certain rights in the invention.

BACKGROUND OF THE INVENTION

Acute respiratory illnesses are extremely common, accounting for more than 500 million outpatient illnesses and 3.6 million hospitalizations per year in the U.S. alone. Viral infection is a common cause of these illnesses but it is usually a diagnosis of exclusion, since currently tests to rule in viral infection are often prohibitive in cost and time. A simple, pan-viral test to rule in a viral cause for respiratory symptoms could have a tremendous positive impact by facilitating rapid diagnosis, improving patient care, and enabling more efficient use of medical resources for the millions of patients with respiratory illness.

Current diagnostic strategies to rule in viral infection require testing for a number of distinct viruses that cause similar symptoms, since tests identify features specific to each virus. Common tests use PCR-based identification of viral genomes or viral antigen detection. Testing for a panel of suspected viruses can be time-consuming and/or expensive, and falsely negative if the patient is infected with a virus that is not in the panel. Identifying which one of many clinically similar viruses is causing a respiratory illness usually does not impact treatment, since virus-specific therapies are only available for influenza.

In addition to facilitating rapid diagnosis and better care of patients with respiratory symptoms, a pan-viral test to rule in viral infection could aid in antimicrobial stewardship. Respiratory infections can be caused by viruses or bacteria, and both types of microorganisms can cause similar clinical symptoms. However, the appropriate treatment for respiratory infection differs significantly depending on the type of organism causing the infection: supportive care is the appropriate treatment for most viral infections, whereas antibiotics, drugs that stop growth of bacteria (but not viruses), can be used to treat bacterial infections. If the cause of respiratory infection is undetermined, often patients will be prescribed bacteria-killing antibiotics. However, there are serious down-sides to prescribing antibiotics when they are not indicated: (1) Inappropriate antibiotic overuse has led to the emergence of antibiotic-resistant bacteria which are a major public health threat, and (2) antibiotic use can eliminate the normal, healthy bacteria present in the patient's body with major health consequences such as promoting life-threatening *C. dificile* colitis. Recent studies show that ~30% of outpatient antibiotic prescriptions are not indicated, and that many of these prescriptions are for patients with non-bacterial respiratory illness, e.g. viral infection of the respiratory tract. In response to the public health impact of these practices, an executive order from President Obama led to the 2015 White House National Action Plan on Antimicrobial Resistance, which calls for a 50% reduction in inappropriate outpatient antibiotic use by 2020. A major objective of the plan is development of better diagnostic tests to distinguish viral from bacterial respiratory infection. The inventions described here would help in this effort, on its own or by being paired with a similar test to rule in bacterial infection.

Therefore there is a need in the art for a practical and reliable test to guide physicians and patients in the decision-making process during suspected respiratory infection. The present invention addresses this need.

SUMMARY OF THE INVENTION

In one aspect the invention provides a method for detecting a respiratory virus in a patient, the method comprising: analyzing a viral transport medium sample to determine a level of at least one nasal virus-induced molecule and a level of a housekeeping gene by measuring mRNA; normalizing the level of the at least one nasal virus-induced molecule to the level of the housekeeping gene to determine a normalized level of the at least one nasal virus-induced molecule; comparing the normalized level of the at least one nasal virus-induced molecule with a predetermined reference level for the at least one nasal virus-induced molecule; and, wherein if the normalized level of the at least one nasal virus-induced molecule is above the respective reference level, the patient is determined to have a respiratory viral infection.

In various embodiments, the mRNA is measured by reverse transcription-qPCR.

In various embodiments, the nasal virus-induced molecule is IFIT1, IFIT2, IFIT3, OASL, OAS1, OAS2, OAS3, ISG15, IFIH1, IFI44, DDX58, DDX60, DDX60L, HERC5, MX1, MX2, IFITM1, RSAD2, IFI44L, IFI27, DHX58 CXCL10, CX3CL1, CXCL8, CXCL11, CXCL1, IL36G, IFNL1, CXCL9, CCL20, IFNL2, CXCL2, TNF, CXCL3 or CCL22.

In various embodiments, the at least one nasal virus-induced molecule comprises OASL, IFIT2 or CXCL10.

In various embodiments, the at least one nasal virus-induced molecule comprises CXCL10 or IFIT2.

In various embodiments, the housekeeping gene comprises β-actin, HPRT, or GAPDH.

In another aspect, the invention provides a method for detecting a respiratory virus in a patient, the method comprising: analyzing a viral transport medium sample to determine a level of at least one nasal virus-induced molecule by measuring protein; comparing the level of the at least one nasal virus-induced molecule with a predetermined reference level for the at least one nasal virus-induced molecule; and, wherein if the level of the at least one nasal virus-induced molecule is above the respective reference level, the patient is determined to have a respiratory viral infection.

In various embodiments, the level of the protein encoded by nasal virus-induced molecule is measured by immunoassay.

In various embodiments, the protein is an interferon or a chemokine.

In various embodiments, the at least one nasal virus-induced molecule is IFIT1, IFIT2, IFIT3, OASL, OAS1, OAS2, OAS3, ISG15, IFIH1, IFI44, DDX58, DDX60, DDX60L, HERC5, MX1, MX2, IFITM1, RSAD2, IFI44L, IFI27, DHX58 CXCL10, CX3CL1, CXCL8, CXCL11, CXCL1, IL36G, IFNL1, CXCL9, CCL20, IFNL2, CXCL2, TNF, CXCL3 or CCL22.

In various embodiments, the at least one Na-VIM is CXCL11, CXCL10, or CXCL9.

In various embodiments, the method further comprises determining the level of IFNL1 as an indicator of sample quality.

In various embodiments, the levels of at least two nasal virus-induced molecules are determined, normalized and compared to the respective reference levels of the nasal virus-induced molecules.

In various embodiments, the level of at least three nasal virus-induced molecules are determined, normalized and compared to the respective reference levels of the nasal virus-induced molecules.

In another aspect the invention provides a method of treating a patient exhibiting symptoms of a respiratory infection, the method comprising: analyzing a viral transport medium sample from the patient to determine a level of at least one nasal virus-induced molecule and a level of a housekeeping gene; normalizing the level of the at least one nasal virus-induced molecule to the level of the housekeeping gene to determine a normalized level of the at least one nasal virus-induced molecule; comparing the normalized level of the at least one nasal virus-induced molecule with a predetermined reference level for the at least one nasal virus-induced molecule; and, wherein if the normalized level of the at least one nasal virus-induced molecule is above the respective reference level, the patient receives treatment for viral infection.

In another aspect, the invention provides a method of treating a patient exhibiting symptoms of a respiratory infection, the method comprising: analyzing a viral transport medium sample from the patient to determine a level of at least one nasal virus-induced molecule and a level of a housekeeping gene; normalizing the level of the at least one nasal virus-induced molecule to the level of the housekeeping gene to determine a normalized level of the at least one nasal virus-induced molecule; comparing the normalized level of the at least one nasal virus-induced molecule with a predetermined reference level for the at least one nasal virus-induced molecule; and, wherein if the normalized level of the at least one nasal virus-induced molecule is above the reference level, the patient is tested for the presence of at least one respiratory virus.

In various embodiments, the method further comprises determining a level of IFNL1 and discarding the sample if the level of IFNL1 is below a predetermined level.

In another aspect the invention provides a kit comprising reagents and primers for detecting a respiratory virus in a patient and instructions for the use thereof, wherein the instructions comprise: analyzing a viral transport medium sample to determine a level of at least one nasal virus-induced molecule and a level of a housekeeping gene; normalizing the level of the at least one nasal virus-induced molecule to the level of the housekeeping gene to determine a normalized level of the at least one nasal virus-induced molecule; comparing the normalized level of the at least one nasal virus-induced molecule with a predetermined reference level for the at least one nasal virus-induced molecule; and, wherein if the normalized level of the at least one nasal virus-induced molecule is above the respective reference level, the patient is determined to have a respiratory viral infection.

In various embodiments, the instructions further comprise determining a level of IFNL1 and discarding the sample if the level of IFNL1 is below a predetermined level.

In another aspect, the invention provides a kit comprising reagents for an immunoassay to detect a respiratory virus in a patient and instructions for the use thereof, wherein the instructions comprise: analyzing a viral transport medium sample to determine a level of at least one protein encoded by a nasal virus-induced molecule; comparing the level of the at least one nasal virus-induced molecule encoded protein with a predetermined reference level for the at least one nasal virus-induced molecule encoded protein; and, wherein if the level of the at least one nasal virus-induced molecule encoded protein is above the respective reference level, the patient is determined to have a respiratory viral infection.

In various embodiments, the instructions further comprise determining a level of IFNL1 and discarding the sample if the level of IFNL1 is below a predetermined level.

In various embodiments, composition comprising at least one biomarker selected from IFIT1, IFIT2, IFIT3, OASL, OAS1, OAS2, OAS3, ISG15, IFIH1, IFI44, DDX58, DDX60, DDX60L, HERC5, MX1, MX2, IFITM1, RSAD2, IFI44L, IFI27, DHX58 CXCL10, CX3CL1, CXCL8, CXCL11, CXCL1, IL36G, IFNL1, CXCL9, CCL20, IFNL2, CXCL2, TNF, CXCL3 or CCL22; wherein the biomarkers have been amplified by performing PCR on mRNA obtained from a viral transport medium sample.

In another aspect, the invention provides a method of determining whether a respiratory virus is involved in an active disease process compared with incidental detection, the method comprising: analyzing a viral transport medium sample from the patient to determine a level of at least one nasal virus-induced molecule and a level of a housekeeping gene; normalizing the level of the at least one nasal virus-induced molecule to the level of the housekeeping gene to determine a normalized level of the at least one nasal virus-induced molecule; comparing the normalized level of the at least one nasal virus-induced molecule with a predetermined reference level for the at least one nasal virus-induced molecule; and, wherein if the normalized level of the at least one nasal virus-induced molecule is above the reference level, the respiratory virus is determined to be in the active disease process.

In another aspect, the invention provides a method for detecting a respiratory virus in a patient, the method comprising: analyzing a viral transport medium sample to determine a level of at least one nasal virus-induced molecule by measuring protein; comparing the level of the at least one nasal virus-induced molecule with a predetermined reference level for the at least one nasal virus-induced molecule; and, wherein if the level of the at least one nasal virus-induced molecule is below the respective reference level, the patient is determined to not have a respiratory viral infection.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2A depicts results from an experiment in which patient cells were pelleted from the transport medium containing patient nasopharyngeal swabs, RNA was isolated, and RT-qPCR was performed for β-actin and three mRNAs associated with the antiviral response as identified in FIG. 1 (OASL, IFIT2, CXCL10). Plots show mRNA levels for 68 samples relative to the mRNA level in resting human nasal epithelial cells (HNEC (−)), sorted by mRNA level for each transcript. Each mRNA biomarker was scored positive if the level was above the level observed in 14 hp-stimulated HNEC, indicated by the dotted line and lowest bar on each graph. mRNA levels were normalized to the level of β-actin mRNA in each sample. Bars in virus column indicate samples which tested positive for respiratory virus by qPCR. Bars marked with an asterisk indicate the five samples that were negative by the initial-virus test panel but positive upon subsequent testing for CoV. FIG. 2B depicts the test performance of mRNA biomarker signature. Samples were scored as biomarker test positive if 2/3 mRNA biomarkers were above the cutoff (dotted lines). FIG. 2C depicts a pie chart which shows the relative abundance of the seven viruses detected in this sample set, representing 28 detections (23 virus positive samples with 5 co-detections.) Virus names are listed in Table 1; CoV=coronavirus OC-43 (only CoV detected). FIG. 2D depicts ROC curves showing predictive value of individual ISG mRNA levels for detection of a respiratory virus in 68 NP swabs (study 1). The relationship between mRNA level and presence of virus was calculated using SPSS statistics.

FIG. 4A depicts the correlation between NP swab CXCL10 and CXCL11 protein levels and detection of respiratory virus in 134 nasopharyngeal swabs tested for respiratory viruses. CXCL10 and CXCL11 levels were measured using magnetic bead immunoassays. Nucleic acids isolated from the viral transport medium were used to test for viruses not on the original test panel, including 4 CoVs and PIV4. Plots show CXCL11 and CXCL10 levels for 134 samples, sorted by CXCL 11 level. Horizontal bar in column labelled virus indicates detection of respiratory virus in the sample; asterisks indicate samples which tested positive for viruses not in the original test panel (Table 1). FIG. 4B depicts ROC curves for CXCL10 and CXCL11 concentrations as predictors of virus detection in this sample set, calculated using SPSS software. FIG. 4C depicts a pie chart showing the types of viruses detected in the 50/134 virus positive samples in study 2. A total of ten distinct viruses were detected, including both influenza A and B and two CoV (OC-43 and 229E.)

FIG. 6A depicts age distribution. FIG. 6B depicts duration of illness. FIG. 6C depicts symptoms reported. FIG. 6D depicts patient gender.

DETAILED DESCRIPTION

Definitions

Figure 1A:
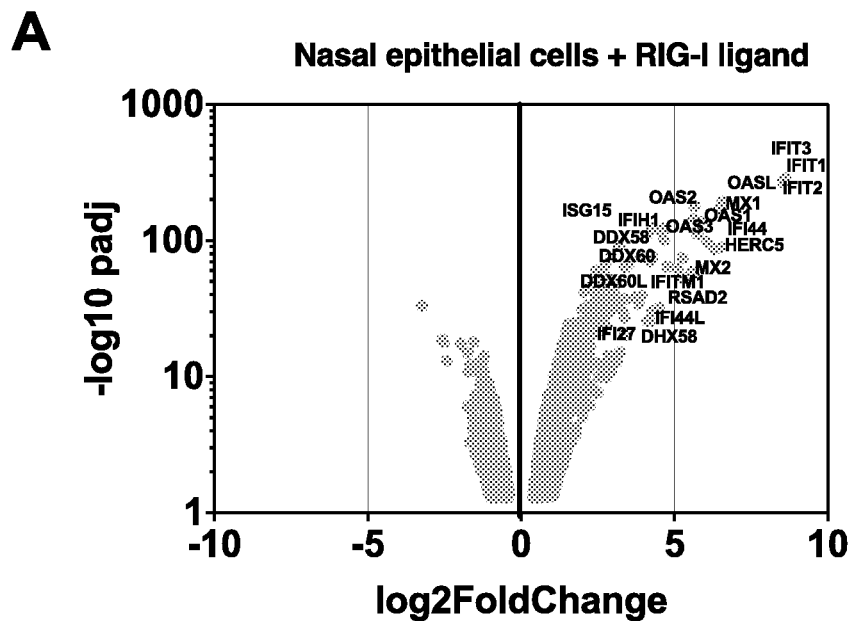
FIG. 1A is a volcano plot depicting induction of host genes in response to RIG-I ligand. The nasal virus-induced molecules (Na-VIMs) currently viewed as the most promising biomarkers in an mRNA based test are named.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The terms "antimicrobial" or "antimicrobial agent" mean any compound with bacteriocidal or bacteriostatic activity which may be used for the treatment of bacterial infection. Non-limiting examples include antibiotics.

"Biological sample" or "sample" as used herein means a biological material isolated from an individual. The biological sample may contain any biological material suitable for detecting the desired biomarkers, and may comprise cellular and/or non-cellular material obtained from the individual. A biological sample may be of any biological tissue or fluid. Frequently the sample will be a "clinical sample" which is a sample derived from a patient. Typical clinical samples include, but are not limited to, bodily fluid samples such as synovial fluid, sputum, blood, urine, blood plasma, blood serum, sweat, mucous, saliva, lymph, bronchial aspirates, peritoneal fluid, cerebrospinal fluid, and pleural fluid, and tissues samples such as blood-cells (e.g., white cells), tissue or fine needle biopsy samples and abscesses or cells therefrom. Biological samples may also include sections of tissues, such as frozen sections or formalin fixed sections taken for histological purposes.

The terms "biomarker" or "marker," as used herein, refers to a molecule that can be detected. Therefore, a biomarker according to the present invention includes, but is not limited to, a nucleic acid, a polypeptide, a carbohydrate, a lipid, an inorganic molecule, an organic molecule, each of which may vary widely in size and properties. A "biomarker" can be a bodily substance relating to a bodily condition or disease. A "biomarker" can be detected using any means known in the art or by a previously unknown means that only becomes apparent upon consideration of the marker by the skilled artisan.

The term "biomarker (or marker) expression" as used herein, encompasses the transcription, translation, post-translation modification, and phenotypic manifestation of a gene, including all aspects of the transformation of information encoded in a gene into RNA or protein. By way of non-limiting example, marker expression includes transcription into messenger RNA (mRNA) and translation into protein. Measuring a biomarker also includes reverse transcription of RNA into cDNA (i.e. for reverse transcription-qPCR measurement of RNA levels.).

As used herein, "biomarker" in the context of the present invention encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. Biomarkers can also include mutated proteins or mutated nucleic acids. Biomarkers also encompass non-blood borne factors or non-analyte physiological markers of health status, such as clinical parameters, as well as traditional laboratory risk factors. As defined by the Food and Drug Administration (FDA), a biomarker is a characteristic (e.g. measurable DNA and/or RNA) that is "objectively measured and evaluated as an indicator of normal biologic processes, pathogenic processes, or pharmacologic responses to a therapeutic intervention or other interventions". Biomarkers also include any calculated indices created mathematically or combinations of any one or more of the foregoing measurements, including temporal trends and differences.

The term "housekeeping gene" refers to a gene where it is practical to normalize the level of other genes against the level of expression of the housekeeping gene in order to control for variables such as, but not limited to, the total amount of biological material in the sample. β-actin is one possible example of a housekeeping gene.

By the phrase "determining the level of expression" is meant an assessment of the absolute or relative quantity of a biomarker in a sample at the nucleic acid or protein level, using technology available to the skilled artisan to detect a sufficient portion of any marker.

As used herein, an "immunoassay" refers to a biochemical test that measures the presence or concentration of a substance in a sample, such as a biological sample, using the reaction of an antibody to its cognate antigen, for example the specific binding of an antibody to a protein. Both the presence of the antigen or the amount of the antigen present can be measured.

As used herein, an "instructional material" includes a publication, a recording, a diagram, or any other medium of expression which can be used to communicate the usefulness of a component of the invention in a kit for detecting biomarkers disclosed herein. The instructional material of the kit of the invention can, for example, be affixed to a container which contains the component of the invention or be shipped together with a container which contains the component. Alternatively, the instructional material can be shipped separately from the container with the intention that the instructional material and the component be used cooperatively by the recipient.

The "level" of one or more biomarkers means the absolute or relative amount or concentration of the biomarker in the sample as determined by measuring mRNA, cDNA or protein, or any portion thereof such as oligonucleotide or peptide.

"Measuring" or "measurement," or alternatively "detecting" or "detection," means determining the presence, absence, quantity or amount (which can be an effective amount) of either a given substance within a clinical or subject-derived sample, including the derivation of qualitative or quantitative concentration levels of such substances, or otherwise determining the values or categorization of a subject's clinical parameters.

"Nasopharyngeal sample" as used herein means any sample from a subject containing RNA or secreted proteins a plurality of which is generated by cells in the upper respiratory tract. Non-limiting examples include nasal swabs, nasopharyngeal swabs, nasopharyngeal aspirate, oral swab, oropharyngeal swab, pharyngeal swabs, throat swabs, or saliva or transport medium exposed to any of these sample types.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "respiratory sample" as used herein means any sample from a subject containing RNA or secreted proteins a plurality of which is generated by cells in the respiratory tract. Non-limiting examples include nasal swabs, nasopharyngeal swabs, nasopharyngeal aspirate, oral swab, oropharyngeal swab, pharyngeal (throat) swab, sputum, bronchoalveolar lavage or saliva or transport medium exposed to any of these sample types.

The term "respiratory virus" as used herein means a virus that can cause or does cause a respiratory virus infection in a patient.

A "reference level" of a biomarker means a level of the biomarker that is indicative of the absence of a particular disease state or phenotype. When the level of a biomarker in a subject is above the reference level of the biomarker it is indicative of the presence of a particular disease state or phenotype. When the level of a biomarker in a subject is within the reference level of the biomarker it is indicative of a lack of a particular disease state or phenotype.

The term "viral transport medium" means a liquid (or liquid at room temperature that is subsequently frozen) used to collect, transport or store viral specimens and maintain their stability.

The term "viral transport medium sample" means viral transport medium that has contacted a respiratory sample or a nasopharyngeal sample. The term may be applied to aliquots taken from viral transport medium that has contacted a respiratory sample or a nasopharyngeal sample.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

In some embodiments the invention is directed to a set of biomarkers that may be analyzed to predict the presence of a respiratory virus infection when their level of expression is measured in samples obtained from a viral transport medium sample. In certain embodiments these markers may be Na-VIMs.

Nasal Virus-Induced Molecules

Figure 1B:
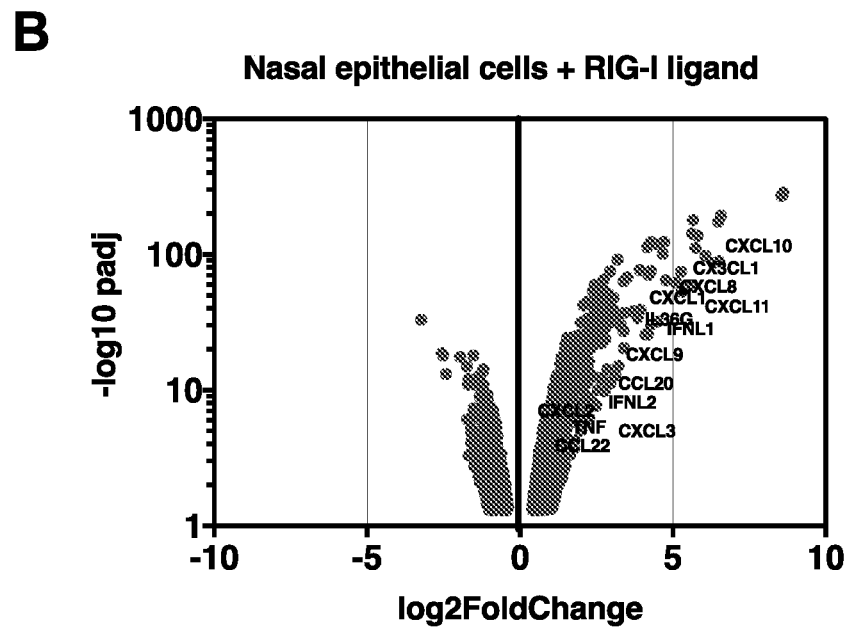
FIG. 1B is a volcano plot depicting induction of host genes in response to RIG-I ligand. The Na-VIMs currently viewed as the most promising biomarkers in an mRNA or protein based test are named.

In some embodiments the invention comprises determining the level of expression of genes which indicate an anti-viral response in the respiratory tract of the patient. These genes and the associated mRNAs and proteins are here called nasal virus-induced molecules (Na-VIMs). Suitable genes were identified according to example 1, and are shown in FIG. 1 and Table 2. The Na-VIMs named in FIGS. 1A and 1B are those that can be used in an mRNA based test. The Na-VIMs named in FIG. 1B are those that can be used in a protein based test, although various embodiments of the invention may encompass measurement of any of these molecules in either test. Examining host genes induced by stimulating the innate immune receptor RIG-I within human nasal epithelial cells reveals biomarkers indicative of infection with diverse respiratory viruses. The invention is not limited to the specific genes recited in the examples as a skilled artisan could identify other suitable genes using the techniques disclosed herein, for example, by using a different ligand to trigger antiviral innate immune responses. In various embodiments, Na-VIMs may be any gene induced during the innate immune reaction of the respiratory tract. Typical genes associated with this class are cytokines, chemokines, interferons, and genes encoding intracellular molecules that function in antiviral defense.

In various embodiments the Na-VIM may be any gene the expression of which changes in a patient having a respiratory viral infection relative to a patient that does not have a respiratory viral infection. In various embodiments the Na-VIM is a chemokine or interferon. In some embodiments the Na-VIM may be any of the genes listed in table 2. In some embodiments the at least one Na-VIM may be selected from IFIT3, IFIT2, IFIT1, OASL, HERC5, MX1, CXCL10, HSPA6, OAS1, IFI44, ISG15, CXCL11, OAS2, CMPK2, MX2, CX3CL1, CXCL8, HSPA1A, DDX58, OAS3, CH25H, IFI44L, IFIH1, IFI6, DDX60, RSAD2, HSPA1B, IFNL1, SAMD9L, ZNF165, IFITM1, IL36G, HELZ2, CXCL1, XAF1, PLAUR, USP18, ZSCAN12P1, APOL1, C110196, HMGCS1, ANGPTL4, THEMIS2, CXCL9, APOL2, DDX60L, ZC3HAV1, CCRN4L, DERL3, SAMD9, SP6, PODXL, HMOX1, PMAP1, PARP9, HERO6, DHX58, NEURL3, CLDN4, DNAJA1, SAMHD1, OSGIN1, CCL20, SP110, TNFAIP3, FGFB8P1, PLA2G4E, IFI35, ATF3, DNAJB4, AKR1C1, GBP4, ZBED2, IFNL2, TRIM21, DNAJA4, IFI27, PTGS2, SEMA7A, HSPA8, HSPH1, BAG3, CYP1A1, DTX3L, MVD, TXNRD1, RHEBL1, IFIT5, IRF1, TRANK1, TNFSF18, MLKL, IRF7, IGFBP6, CRYAB, PLEKHA4, DNAJB1, PLA2G3, RGS2, S1PR3, HCAR2, PRR15, AKR1B10, CXCL3, SLC9B1, NAV3, ISG20, STARD5, CYP27B1, APLN, IRF9, CYP26B1, HSP90AA1, PCSK9, EPSTI1, ADAMTS15, TNFSF10, GBP5, KRT34 and TNF. In some embodiments the Na-VIM is selected from IFIT1, IFIT2, IFIT3, OASL, OAS1, OAS2, OAS3, ISG15, IFIH1, IFI44, DDX58, DDX60, DDX60L, HERC5, MX1, MX2, IFITM1, RSAD2, IFI44L, IFI27, DHX58, CXCL10, CX3CL1, CXCL8, CXCL11, CXCL1, IL36G, IFNL1, CXCL9, CCL20, IFNL2, CXCL2, TNF, CXCL3 or CCL22.

"Rule in" or "rule out" tests (with threshold set for high positive predictive value or high negative predictive value respectively) support appropriate medical decision making and efficient utilization of resources when well-understood by health care providers. Extensive host signatures are not required for sensitive, specific, and accurate diagnosis of respiratory virus infection when employing the presently disclosed techniques. Studies to diagnose respiratory virus infection from the blood transcriptome have described patterns of host gene expression that can discriminate the cause of infection but require measurement of tens or hundreds of mRNAs, or in some cases of the whole transcriptome. Surprisingly, the performance of a prospective test based on only three mRNA levels as described in the examples below was robust (FIG. 2); and could be replicated using only two mRNA levels after retrospective analysis. mRNA and protein levels of certain Na-VIMs measured in NP swabs correlate directly with the presence of a respiratory virus infection, are more practical for adaptation as a laboratory based or point of care test and require analysis of a far smaller number of biomarkers than other approaches which attempt to determine the cause of respiratory infection based on the host response. The results herein disclosed show, for multiple biomarkers, that the quantitative level of mRNA or protein was diagnostically useful: high levels indicated the presence of virus, low levels indicated absence, with few or no exceptions for many of the biomarkers tested. This allows the development of robust "rule in" or "rule out" tests useful for diagnosis of virus infection in a large percentage of patients using a single biomarker. Various embodiments comprise a method to rule in respiratory viral infection using only a single Na-VIM as a biomarker but other embodiments may comprise determining the level of two, three or more Na-VIMs.

Figure 10:
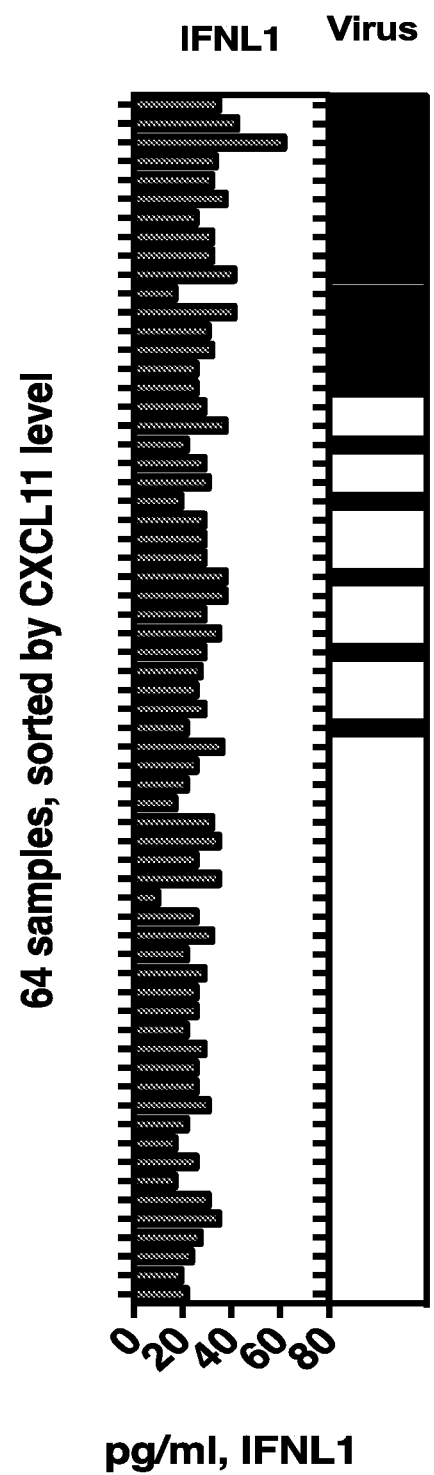
FIG. 10. depicts Interferon Lambda-1 protein level in 64 NP swabs (sorted by CXCL11 level as shown in FIG. 3), and the bars in the virus column indicate presence of virus.

In certain embodiments comprising determining the level of two or more Na-VIMS, the level of one or more of the Na-VIMs may be measured as an indicator of sample quality. The absence or relative absence of certain Na-VIMs is an indication that the sample is of poor quality and should be discarded. In certain embodiments, the Na-VIM used as an indicator of sample quality may be IFNL1. This point is illustrated in FIG. 10.

Method of Detecting Respiratory Viral Infection by Analyzing Viral Transport Medium Used to Contain Nasopharyngeal Samples In various embodiments the invention is directed to a method of detecting viral infection by collecting patient cells, cell debris, or cell free fluid from viral transport medium samples and determining the level at least one Na-VIM and comparing the level of the Na-VIM with its respective reference level. Various embodiments include a method of detecting respiratory viral infection in viral transport medium samples by measuring increased expression of various Na-VIMs relative to reference levels determined by measuring the respective level of the Na-VIMs in uninfected patients. The present disclosure teaches that it is possible to detect relevant host responses by measuring mRNA or protein in a viral transport medium sample.

In some embodiments the viral transport medium samples are prepared by placing a respiratory sample in viral transport medium and releasing material from the respiratory sample into the viral transport medium. In various embodiments the respiratory sample used to create the viral transport medium sample may be obtained from the upper respiratory tract. In other embodiments the nasopharyngeal sample used to create the viral transport medium sample may be obtained from the lower respiratory tract.

In some embodiments the viral transport medium samples are prepared by placing an nasopharyngeal sample in viral transport medium and releasing material from the nasopharyngeal sample into the viral transport medium. Release of the material may be aided by stirring, vortexing or any other method known in the art or may simply occur by passive diffusion. The viral transport medium may be of any type known in the art and may comprise various additives to stabilize viruses, proteins or other biological materials including but not limited to pH buffers, antibiotics, and/or cryoprotectants such as sucrose. A non-limiting example is BD' universal virus transport medium.

Unexpectedly, markers for host response to viral infection are easily detectable in this sample type. Samples obtained by sampling the nasopharynx are much less invasive and are more directly relevant to disease pathogenesis than blood samples in the case of respiratory infection. Finding that this sample type can be used for host response studies dramatically improves the prospects for developing practical laboratory based and/or point-of-care tests based on measurement of protein or mRNA in viral transport medium. Accordingly, in some embodiments expression of biomarkers is determined by measuring mRNA. In other embodiments, expression is determined by measuring protein.

Figure 3:
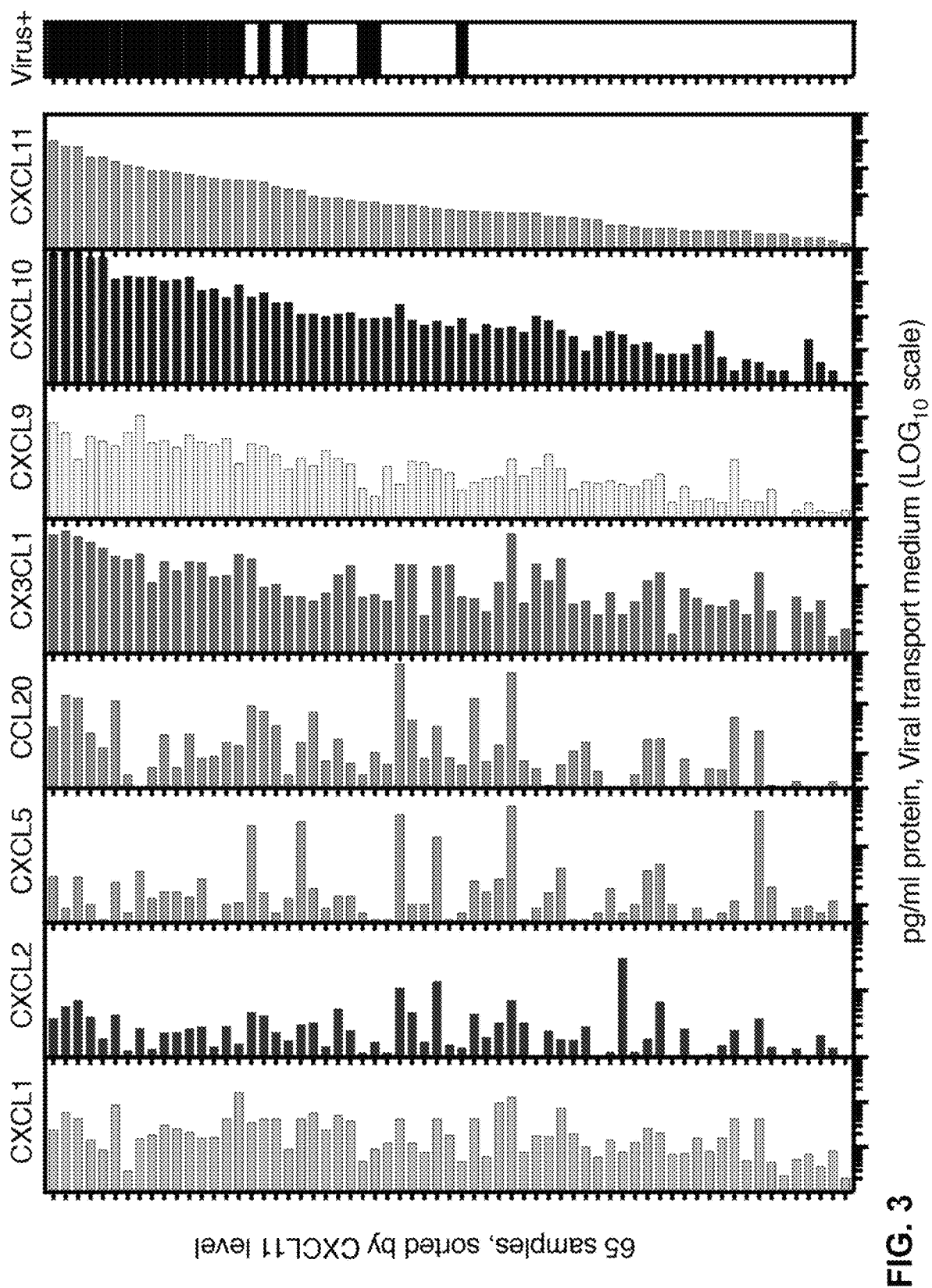
FIG. 3 depicts protein levels of eight chemokines in the NP-swab associated viral transport medium and their relationship to virus detection (study 1). Levels of eight chemokines were measured in the viral transport medium associated with 65 NP swabs from the study described in FIG. 2, using magnetic bead immunoassays. For graph, all samples (1-65) are sorted based on CXCL11 level. Bars (right panel) indicate which samples also tested positive for a respiratory virus. Protein concentrations are plotted on a log scale across the following ranges: CXCL1($10^2$-$10^5$), CXCL2 (10-$10^5$), CCL20 (1-$10^3$), CX3CL1 (10-$10^3$), CXCL10(10-$10^5$), CXCL11 (1-$10^5$).

In embodiments comprising the measurement of protein, the viral transport medium may be used in an immunoassay. The high diagnostic accuracy of a test based on immunoassays as measured in samples of viral transport medium is shown in FIGS. 3 and 4. In various embodiments the proteins are secreted proteins, in some embodiments the proteins are chemokines. In certain embodiments, the method is carried out by determining the level of Na-VIMs by analyzing RNA isolated from viral transport medium samples that have contained nasopharyngeal samples. In some embodiments the level of the at least one Na-VIM is determined by measuring protein encoded by CXCL10, CX3CL1, CXCL8, CXCL11, CXCL1, IL36G, IFNL1, CXCL9, CCL20, IFNL2, CXCL2, TNF, CXCL3 or CCL22.

In embodiments comprising the measurement of mRNA, the viral transport medium may be centrifuged to form a pellet of cells and cell debris which is then added to lysis buffer. Total nucleic acid is isolated from the pellet and DNA is digested using, by way of non-limiting example, DNAse I. The RNA is then reverse transcribed into cDNA. The cDNA is then analyzed to determine the level of at least one Na-VIM. In some embodiments the level of the at least one Na-VIM is determined by reverse transcription quantitative polymerase chain reaction (rt-qPCR) although the skilled artisan will appreciate that there are other ways that the level of the at least one Na-VIM may be determined by the analysis of mRNA and these methods are encompassed by the invention in its various embodiments. A skilled person is capable of selecting and practicing an appropriate technique as the measurement of levels of specific mRNAs and proteins in a sample is a familiar operation to a skilled artisan. In some embodiments the level of the at least one Na-VIM determined by measuring mRNA is IFIT1, IFIT2, IFIT3, OASL, OAS1, OAS2, OAS3, ISG15, IFIH1, IFI44, DDX58, DDX60, DDX60L, HERC5, MX1, MX2, IFITM1, RSAD2, IFI44L, IFI27, DHX58 CXCL10, CX3CL1, CXCL8, CXCL11, CXCL1, IL36G, IFNL1, CXCL9, CCL20, IFNL2, CXCL2, TNF, CXCL3 or CCL22. In some embodiments mRNA levels can be assessed using nucleic acids isolated directly from the viral transport medium.

In some embodiments, the expression level of the measured Na-VIMs are normalized to the expression level of a housekeeping gene. The expression level of the housekeeping gene may be measured using the same method as the one or more Na-VIMs. In some embodiments, the housekeeping gene is β-actin, HPRT, or GAPDH.

In various embodiments, there is provided a composition comprising amplified polynucleotides corresponding to two or more biomarkers corresponding to the Na-VIMs described herein. In these embodiments the amplified polynucleotides are generated by performing reverse-transcription qPCR on RNA isolated from nasopharyngeal samples. In some aspects, the composition further comprises an amplified polynucleotide encoding a housekeeping gene. In certain embodiments, the housekeeping gene may be β-actin.

A method of reducing the inappropriate use of antibiotics in a medical facility is also included. The method comprises determining the level of at least one Na-VIM in a nasopharyngeal sample obtained from a patient and comparing the level of the Na-VIM with a previously determined cutoff reflecting the reference level. Wherein when the level of the Na-VIM exceeds the cutoff, the patient and physician are educated about the meaning of the test result and inappropriate use of antimicrobial agents to treat the patient is discouraged.

In various embodiments the level of IFNL1 may be used as an indicator of sample quality, samples with a level of IFNL1 below a cutoff level may be discarded as lacking diagnostic utility. In some embodiments, the method further comprises the step of additional virology testing (e.g. for influenza virus) on patients in whom viral infection is indicated based on the initial test result. The consistent level of IFNL1 in uncompromised viral transport medium samples is depicted in FIG. 10.

Some embodiments comprise a method of treating a patient exhibiting symptoms of respiratory viral infection comprising determining levels of Na-VIM by measuring either protein or mRNA. In various embodiments, patients exhibiting a level of the biomarker may be treated for respiratory viral infection or may be tested for specific respiratory viruses, by way of nonlimiting example, influenza virus.

Figure 9:
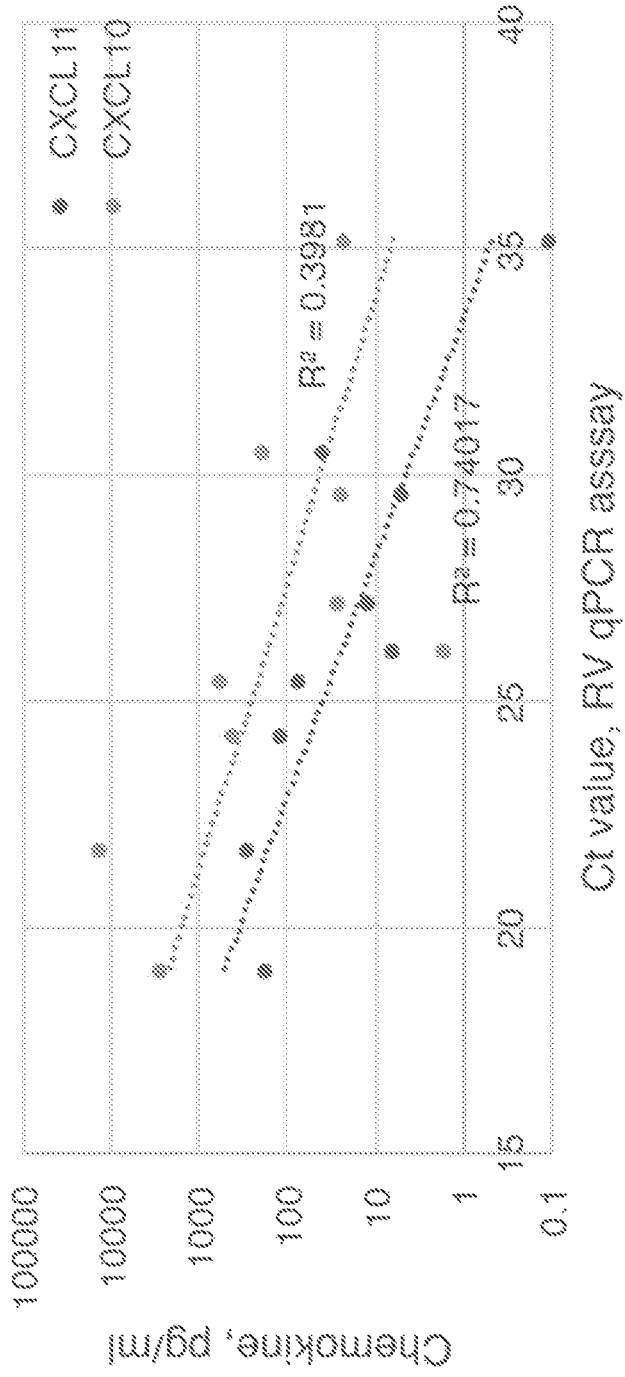
FIG. 9. depicts correlation between Chemokine concentration (y-axis) and Ct value in RT-qPCR assay for rhinovirus genome detection (X-axis). Low Ct values correlate with higher levels of virus (Ct value=cycle threshold at which PCR product is detected.) R-squared values for exponential curve fits were calculated in Excel.

In recent years epidemiological surveys testing for a panel of respiratory viruses have repeatedly found high rates of respiratory virus detection even in the asymptomatic population. This calls into question the usefulness of sensitive PCR-based tests for viral genomes to pinpoint viral infection as a cause of disease; clearly, the test can be positive in the absence of disease. In such cases, the host-response based test described here may also be useful in differentiating a respiratory virus infection as the immediate cause of illness from incidental presence of viral genomes in the nasopharynx. The reference level may be set such that it indicates that a respiratory virus is the cause for the patient's symptoms. Accordingly, in one aspect the invention provides a method of determining whether a respiratory virus is involved in an active disease process compared with incidental detection. This aspect of the invention is illustrated in FIG. 9. FIG. 9 compares the levels CXCL10 and CXCL11 to the count value of a rhinovirus as measured in a qPCR assay.

The present invention partially addresses a long felt need for a practical means to rule in or rule out infection with a respiratory virus in general, without requiring testing for individual viruses. Such a test would aid in rapid diagnosis of respiratory infections and improve patient care and cost-effectiveness of health care for patients with respiratory or non-specific symptoms. In addition, the invention addresses a need for tests to discriminate between bacterial infection, where antibiotic treatment is appropriate, and viral infection where antibiotics are not appropriate. The current standard of care for "ruling in" respiratory virus infection requires testing with a panel of virus-specific tests. In addition to issues of cost and turn-around-time, virus panels lack sensitivity if the virus the patient has is not represented on the panel. Furthermore, for some viruses, such as emerging respiratory pathogens, there are no virus-specific tests available; in fact, in the case of an epidemic respiratory syndrome, even the type of disease process (e.g., bacterial infection vs. viral infection vs. toxin) may be unknown. For all of these reasons, a practical general test detecting that the patient's respiratory tract is responding to a viral infection would fill an unmet need.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in the experiments disclosed herein are now described.

Nasal Epithelial Cell Culture and Stimulation with Viral-Mimetic Ligand 14 hp.

Primary human nasal epithelial cells were obtained from organ donors (Promocell, Germany) and grown to 80% confluence on collagen-coated tissue culture dishes using complete bronchial epithelia growth medium (BEGM, Lonza). Hydrocortisone and epinephrine supplements were removed from medium 2 days prior to stimulation. Cells were transfected with the small RNA hairpin ligand for RIG-I, 14 hp, by complexing with Lipofectamine 2000 (Invitrogen 1168-019). After 1 hr stimulation, lipofectamine mixture was removed, medium was re-added, and cells were incubated for 7 additional hours at 37° C.

RNASeq

RNA was isolated from 14 hp-treated or untreated primary nasal epithelial cells as above and used to generate libraries which were sequenced on the Illumina Hi-Seq 2000® using pair-end sequencing at the Yale Center for Genomic Analysis. Standard bioinformatics techniques were employed for data analysis.

Study Design

Sample selection: Study 1 (mRNA qPCR testing and sample scoring) was performed on 68 NP swabs sent to the Yale New Haven Hospital (YNHH) clinical laboratory for comprehensive respiratory viruses testing during 14 designated days. NP swabs were included if (1) entire test panel was ordered, including DFA testing, (2) samples arrived between 8 AM-4 PM (stored for a maximum of 8 hr at 4° C.), (3) samples were of sufficient quality to perform all standard virology assays (89.9% of samples received on these days). Samples were de-identified according to the guidelines for non-human subjects research.

Study 2 (immunoassay testing) was performed on viral transport medium from 134 NP swabs sent to the YNHH lab and stored frozen until the study was performed. For both studies, samples were included if (1) both direct fluorescent antigen (DFA) testing and the 9-virus respiratory PCR panel was ordered and (2) the samples were of sufficient quality to perform DFA testing as determined by microscopy (~90% of samples). Protocol was approved by the Yale Human Investigations Committee.

Assessing performance of Na-VIM mRNA and chemokine ELISA tests: The investigator performing Na-VIM qPCR testing did not have access to patient information; all samples were de-identified and coded by the clinical laboratory. Na-VIM testing was performed and samples were scored as positive or negative prospectively. A different investigator performed chart review and recorded clinical data and virology test results. Once patient results and Na-VIM test results had been separately recorded, study was un-blinded and analysis of test performance was performed, as was multiplex PCR testing for coronaviruses as described below. ELISA testing for chemokines in VTM was performed retrospectively as described in the text (results known.)

Clinical virology testing. Samples were received from throughout the YNHH system using flocked swabs placed into 3 ml universal viral transport medium (BD universal viral transport kit, Cat no. 220528) PCR and direct fluorescent antigen testing for a panel of nine respiratory viruses was performed (See Table 1 for list of viruses). Lab-developed PCR tests for respiratory viruses listed in Table 1 were performed on nucleic acids isolated from 0.2 ml of viral transport medium using the bioMerieux Nuclisens (Boom method) on the Easy Mag instrument. DFA tests were performed on cells pelleted from the viral transport medium and resuspended in PBS per manufacturer's protocols using commercial reagents. PCR and direct fluorescent antigen testing for a panel of nine respiratory viruses were performed as previously described in the literature.

TABLE 1

Respiratory virus tests in the Yale-New Haven hospital panel

Adenovirus[1,2]
Human metapneumovirus[1,2]
Influenza A and B[1,2]
Parainfluenza 1, 2, and 3[1,2]
Respiratory syncitial virus[1,2]
Rhinovirus[1]

[1]Semi quantitative qPCR; [2]Direct fluorescent antigen testing

Quantitative RT-PCR for Na-VIMs. After clinical testing was complete, NP-swab associated cells were stored for up to 1 hr at RT or up to 8 hr at 4° C., then pelleted from viral transport medium and resuspended in 0.35 ml RLT lysis buffer, then frozen at −80° C. for later RNA isolation. RNA was isolated using the RNeasy KIT (Qiagen) and reverse-transcribed RNA using iSCRIPT cDNA synthesis kit (Bio-Rad, Hercules, CA). A wide range of nucleic acid concentrations, ranging from 5-300 were obtained per sample.

QPCR was performed using iTAQ Universal SYBR Green (Biorad). Primer sequences were:

```
βACTIN
(F: SEQ ID NO. 1 CCTGGCACCCAGCACAAT;
R: SEQ ID NO. 2 GCCGATCCACACGGAGTACT)

OASL
(F: SEQ ID NO. 3 AAGGTAGTCAAGGTGGGCTC;
R: SEQ ID NO. 4 CTCCTGGAAGCTGTGGAAAC)

IFIT2
(F: SEQ ID NO. 5 CCTCAAAGGGCAAAACGAGG;
R: SEQ ID NO. 6 CTGATTTCTGCCTGGTCAGC)

CXCL10
(F: SEQ ID NO. 7 CCTGCAAGCCAATTTTGTCC
R: SEQ ID NO. 8 ATGGCCTTCGATTCTGGATTC)
```

For coronavirus multiplex PCR assay primer sequences (from Arvia et al, Molecular and Cellular Probes (2015)29: 408-413) for CoV-NL63, CoV-229E, CoV-0C43, and CoV-SARS were used, as well as primers designed to a different region of the CoV-0C43 genome. CoV 0C43 primers included:
CoV OC-43 nucleocapsid (from Arvia et al)

```
(F: SEQ ID NO. 9 CGATGAGGCTATTCCGACTAGGT;
R: SEQ ID NO. 10 CCTTCCTGAGCCTTCAATATAGTAACC)

CoV OC-43 NSP1
(F: SEQ ID NO. 11 GAGCTTGAAGGTGTAGGTGC;
R: SEQ ID NO. 12 CAAGAACTTCCTCGCCAGC)
```

For study 1, CoV testing was performed on RNA isolated from cell pellets. For Study 2, CoV and PIV4 testing was performed on nucleic acid isolated from viral transport medium bioMerieux Nuclisens (Boom method), followed by gDNA digestion and reverse transcription (iScript gDNA clear, BioRad). PIV4 testing was performed as previously reported in the literature.

Immunoassays for secreted proteins in viral transport medium: Upon receipt of NP swabs in universal viral transport medium, clinical laboratory personnel briefly vortexed the swab/medium tube and removed 0.5-1 ml of medium for storage at −80° C. To perform immunoassays, these aliquots were thawed on ice, spun at 400 g×5 min at 4° C. to remove cell debris, and supernatant was transferred to a 96 well plate. Multiplex immunoassays were performed using the Bio Rad Bio-Plex instrument using Milliplex MAP human cytokine panel III (HCYP3MAG-63K) or Bio-Plex Pro Human Chemokine panel per manufacturer's instructions. Chemokine levels were measured in undiluted samples; results reported for CXCL10 and CXCL11 were based on measurements from both undiluted samples and 1:5 dilutions of samples in transport medium.

Data analysis and statistics. Data analysis of test performance metrics was performed using IBM SPSS and SAS/STAT statistical analysis software.

Example 1: RIG-I Stimulation Triggers Induction of Interferon-Stimulated Genes Including Chemokines in Human Nasal Epithelial Cells The transcriptional response of primary human nasal epithelial cells (HNEC) stimulated in vitro with a specific small molecule ligand of RIG-I (14 hp), a cytoplasmic receptor for viral RNA known to trigger antiviral innate immune responses in respiratory epithelial cells, was examined. RNA was isolated from nasal cells after stimulation with 14 hp and incubation at 37° C. for 8 hr., and transcriptome changes were examined using RNASeq (FIG. 1 and Table 2). Examination of the most significantly induced transcripts (log 2FoldChange>2, p>0.05) revealed some overlap with respiratory virus infection-associated signatures previously identified from the blood transcriptome, such as interferon-stimulated genes encoding intracellular or transmembrane antiviral defense proteins, such as the IFIT genes, OAS genes, and RSAD2/viperin (Table 2). Na-VIM also included genes specific to the response to viral infection within the infected tissue, such as chemokines, and genes that are not considered interferon stimulated genes.

TABLE 2

Transcripts induced by 14 hp in nasal epithelial cells [log2 FC > 2, p < 0.05]
*sorted by Log2Fold Change

| | | name | log2FoldChange* | padj |
|---|---|---|---|---|
| 1 | ENSG00000119917 | IFIT3 | 8.611393418 | 8.0924E−287 |
| 2 | ENSG00000119922 | IFIT2 | 8.590190005 | 6.6884E−275 |
| 3 | ENSG00000185745 | IFIT1 | 8.546567665 | 4.4263E−270 |
| 4 | ENSG00000135114 | OASL | 6.572461394 | 1.3962E−193 |
| 5 | ENSG00000138646 | HERC5 | 6.510793036 | 8.39773E−90 |
| 6 | ENSG00000157601 | MXI | 6.487847248 | 2.3677E−174 |
| 7 | ENSG00000169245 | CXCL10# | 6.318573752 | 3.54056E−87 |
| 8 | ENSG00000173110 | HSPA6 | 6.071703284 | 1.54506E−98 |
| 9 | ENSG00000089127 | OASI | 5.808443795 | 4.2228E−138 |
| 10 | ENSG00000137965 | IFI44 | 5.742808112 | 1.2311E−112 |
| 11 | ENSG00000187608 | ISG15 | 5.659229306 | 6.5815E−180 |
| 12 | ENSG00000169248 | CXCL11 | 5.642394328 | 3.53198E−58 |
| 13 | ENSG00000111335 | OAS2 | 5.632369276 | 3.0725E−143 |
| 14 | ENSG00000134326 | CMPK2 | 5.581856338 | 7.73411E−60 |
| 15 | ENSG00000183486 | MX2 | 5.282207919 | 6.94324E−54 |
| 16 | ENSG00000006210 | CX3CL1 | 5.270156491 | 2.45627E−75 |
| 17 | ENSG00000161570 | NA | 5.109274183 | 1.30602E−62 |
| 18 | ENSG00000169429 | CXCL8 | 4.771849114 | 4.65035E−65 |
| 19 | ENSG00000204389 | HSPA1A | 4.713080209 | 1.8264E−124 |
| 20 | ENSG00000107201 | DDX58 | 4.666164824 | 7.5314E−102 |
| 21 | ENSG00000111331 | 0AS3 | 4.506616219 | 1.0547E−119 |
| 22 | ENSG00000138135 | CH25H | 4.505207533 | 1.11172E−32 |
| 23 | ENSG00000137959 | IFI44L | 4.288815032 | 4.09136E−31 |
| 24 | ENSG00000115267 | IFIH1 | 4.276995899 | 3.8088E−124 |
| 25 | ENSG00000126709 | IFI6 | 4.274630573 | 3.3313E−76 |
| 26 | ENSG00000137628 | DDX60 | 4.201802303 | 3.55189E−71 |
| 27 | ENSG00000134321 | RSAD2 | 4.18430399 | 2.72845E−26 |
| 28 | ENSG00000204388 | HSPA1B | 4.15467765 | 1.1595E−113 |
| 29 | ENSG00000182393 | IFNL1 | 4.104481699 | 1.77067E−26 |

TABLE 2-continued

Transcripts induced by 14 hp in nasal epithelial cells [log2 FC > 2, p < 0.05]
*sorted by Log2Fold Change

|  | name | log2FoldChange* | padj |
|---|---|---|---|
| 30 ENSG00000177409 | SAMD9L | 3.936210162 | 7.31532E-40 |
| 31 ENSG00000197279 | ZNF165 | 3.912907427 | 3.65517E-77 |
| 32 ENSG00000185885 | IFITM1 | 3.840045518 | 8.65309E-35 |
| 33 ENSG00000136688 | IL36G | 3.702192698 | 7.67828E-39 |
| 34 ENSG00000130589 | HELZ2 | 3.516215066 | 2.3625E-68 |
| 35 ENSG00000163739 | CXCL1 | 3.413686517 | 5.36081E-38 |
| 36 ENSG00000132530 | XAF1 | 3.40555388 | 4.13208E-21 |
| 37 ENSG00000011422 | PLAUR | 3.391937461 | 5.47207E-64 |
| 38 ENSG00000184979 | USP18 | 3.387705708 | 6.78695E-28 |
| 39 ENSG00000219891 | ZSCAN12P1 | 3.303030038 | 6.82501E-31 |
| 40 ENSG00000100342 | APOL1 | 3.238506383 | 2.62835E-36 |
| 41 ENSG00000187479 | C11orf96 | 3.221151972 | 1.93618E-16 |
| 42 ENSG00000112972 | HMGCS1 | 3.192285269 | 1.93618E-92 |
| 43 ENSG00000225886 |  | 3.117579963 | 1.76263E-13 |
| 44 ENSG00000167772 | ANGPTL4 | 3.053803007 | 1.05491E-48 |
| 45 ENSG00000130775 | THEMIS2 | 3.045362221 | 2.97613E-40 |
| 46 ENSG00000171658 |  | 3.038243171 | 1.9582E-37 |
| 47 ENSG00000138755 | CXCL9 | 2.946997696 | 6.69733E-12 |
| 48 ENSG00000128335 | APOL2 | 2.941400567 | 1.17379E-38 |
| 49 ENSG00000181381 | DDX60L | 2.936461875 | 3.03477E-32 |
| 50 ENSG00000105939 | ZC3HAV1 | 2.934710141 | 8.96635E-76 |
| 51 ENSG00000151014 | CCRN4L | 2.903097301 | 8.26633E-52 |
| 52 ENSG00000099958 | DERL3 | 2.897951499 | 5.14317E-12 |
| 53 ENSG00000205413 | SAMD9 | 2.877054429 | 1.94228E-51 |
| 54 ENSG00000189120 | SP6 | 2.871144946 | 8.56774E-38 |
| 55 ENSG00000128567 | PODXL | 2.851317991 | 6.3031E-15 |
| 56 ENSG00000100292 | HMOX1 | 2.840815696 | 1.92374E-35 |
| 57 ENSG00000141682 | PMAIP1 | 2.830315653 | 8.78128E-47 |
| 58 ENSG00000138496 | PARP9 | 2.802103683 | 1.5754E-38 |
| 59 ENSG00000138642 | HERC6 | 2.799796856 | 8.18589E-30 |
| 60 ENSG00000108771 | DHX58 | 2.789478112 | 2.43823E-24 |
| 61 ENSG00000163121 | NEURL3 | 2.776954555 | 1.48199E-10 |
| 62 ENSG00000189143 | CLDN4 | 2.755877189 | 9.2026E-55 |
| 63 ENSG00000086061 | DNAJA1 | 2.739240757 | 7.08919E-66 |
| 64 ENSG00000101347 | SAMHD1 | 2.721364022 | 4.7381E-29 |
| 65 ENSG00000140961 | OSGIN1 | 2.713640363 | 6.69915E-28 |
| 66 ENSG00000115009 | CCL20 | 2.690955377 | 9.17888E-13 |
| 67 ENSG00000135899 | SP110 | 2.668243491 | 6.01498E-23 |
| 68 ENSG00000118503 | TNFAIP3 | 2.618602007 | 2.24691E-47 |
| 69 ENSG00000137440 | FGFBP1 | 2.616786101 | 4.02828E-55 |
| 70 ENSG00000188089 | PLA2G4E | 2.608616398 | 1.9524E-29 |
| 71 ENSG00000068079 | IFI35 | 2.592919524 | 6.32258E-13 |
| 72 ENSG00000162772 | ATF3 | 2.559420419 | 2.51983E-45 |
| 73 ENSG00000162616 | DNAJB4 | 2.555555705 | 5.14465E-35 |
| 74 ENSG00000187134 | AKR1C1 | 2.542023649 | 6.39604E-49 |
| 75 ENSG00000162654 | GBP4 | 2.541816929 | 1.07087E-10 |
| 76 ENSG00000177494 | ZBED2 | 2.535147299 | 4.85976E-38 |
| 77 ENSG00000183709 | IFNL2 | 2.499041782 | 2.20438E-08 |
| 78 ENSG00000132109 | TRIM21 | 2.488613569 | 1.25783E-30 |
| 79 ENSG00000140403 | DNAJA4 | 2.478277958 | 1.04075E-35 |
| 80 ENSG00000165949 | IFI27 | 2.477657733 | 2.83077E-25 |
| 81 ENSG00000073756 | PTGS2 | 2.455821223 | 2.83713E-44 |
| 82 ENSG00000138623 | SEMA7A | 2.450990336 | 6.19567E-23 |
| 83 ENSG00000109971 | HSPA8 | 2.447750889 | 2.20817E-60 |
| 84 ENSG00000120694 | HSPH1 | 2.440302922 | 1.17834E-57 |
| 85 ENSG00000151929 | BAG3 | 2.423737369 | 1.05376E-40 |
| 86 ENSG00000140465 | CYP1A1 | 2.412510313 | 2.37912E-13 |
| 87 ENSG00000163840 | DTX3L | 2.406938634 | 3.95996E-34 |
| 88 ENSG00000167508 | MVD | 2.401189413 | 3.40212E-34 |
| 89 ENSG00000198431 | TXNRD1 | 2.38875565 | 1.64952E-54 |
| 90 ENSG00000167550 | RHEBL1 | 2.359181176 | 6.53414E-09 |
| 91 ENSG00000152778 | IFIT5 | 2.347074985 | 2.39126E-21 |
| 92 ENSG00000125347 | IRF1 | 2.291266282 | 1.85002E-30 |
| 93 ENSG00000168016 | TRANK1 | 2.252761942 | 4.53137E-17 |
| 94 ENSG00000120337 | TNFSF18 | 2.250579731 | 6.82592E-07 |
| 95 ENSG00000223935 |  | 2.241236275 | 6.00436E-07 |
| 96 ENSG00000168404 | MLKL | 2.240987584 | 1.22264E-13 |
| 97 ENSG00000185507 | IRF7 | 2.234524482 | 3.63184E-28 |
| 98 ENSG00000167779 | IGFBP6 | 2.222785216 | 4.87496E-15 |
| 99 ENSG00000109846 | CRYAB | 2.221707038 | 1.99691E-34 |
| 100 ENSG00000105559 | PLEKHA4 | 2.209601971 | 3.20247E-13 |
| 101 ENSG00000132002 | DNAJB1 | 2.206343905 | 1.58851E-45 |
| 102 ENSG00000100078 | PLA2G3 | 2.204713476 | 1.26546E-09 |
| 103 ENSG00000116741 | RGS2 | 2.197991412 | 5.78742E-20 |
| 104 ENSG00000213694 | S1PR3 | 2.185018535 | 7.08002E-12 |
| 105 ENSG00000182782 | HCAR2 | 2.165274962 | 5.66981E-24 |
| 106 ENSG00000176532 | PRR15 | 2.132984445 | 4.97601E-09 |
| 107 ENSG00000198074 | AKR1B10 | 2.122087475 | 2.51265E-23 |
| 108 ENSG00000163734 | CXCL3 | 2.121552019 | 1.042E-06 |
| 109 ENSG00000164037 | SLC9B1 | 2.118265209 | 3.83902E-08 |
| 110 ENSG00000067798 | NAV3 | 2.115830862 | 4.32163E-13 |
| 111 ENSG00000172070 | NA | 2.111578289 | 3.51243E-24 |
| 112 ENSG00000172183 | ISG20 | 2.107737929 | 1.20812E-18 |
| 113 ENSG00000172345 | STARD5 | 2.105608091 | 1.71919E-17 |
| 114 ENSG00000111012 | CYP27B1 | 2.102796262 | 2.85924E-07 |
| 115 ENSG00000171388 | APLN | 2.099746107 | 1.31398E-06 |
| 116 ENSG00000213928 | IRF9 | 2.080634106 | 2.79982E-07 |
| 117 ENSG00000003137 | CYP26B1 | 2.079945124 | 1.88765E-10 |
| 118 ENSG00000080824 | HSP90AA1 | 2.068021537 | 7.59429E-43 |
| 119 ENSG00000169174 | PCSK9 | 2.03686705 | 3.37339E-22 |
| 120 ENSG00000133106 | EPSTI1 | 2.017437627 | 7.76823E-11 |
| 121 ENSG00000166106 | ADAMTS15 | 2.013190027 | 1.45721E-06 |
| 122 ENSG00000121858 | TNFSF10 | 2.009456533 | 8.37626E-21 |
| 123 ENSG00000154451 | GBP5 | 2.007765986 | 3.01938E-12 |
| 124 ENSG00000131737 | KRT34 | 2.001121049 | 1.6089E-16 |
| 125 ENSG00000232810 | TNF | 2.001088312 | 9.22284E-06 | known secreted proteins are highlighted

With a view towards ultimately developing a practical, immunoassay-based laboratory and/or point-of-care test, the list of most significantly induced transcripts for mRNAs encoding known secreted proteins measurable by immunoassay were examined (FIG. 1B; Table 2). Of 12 transcripts identified (highlighted in Table 2), 2 encode Type III interferons (IFNL1 and IFNL2), and 7 encode chemokines, small secreted proteins that function as chemoattractants to recruit cells of the immune system to infected tissues. Chemokine induction in nasal epithelial cells fits with their biological role in the target tissue during viral infection, where they attract cells of the immune system to sites of infection.

Example 2: Transcriptional Signature Based on Three Na-VIM mRNAs Predicts Respiratory Virus Infection in NP Swabs Next, it was investigated whether examining a minimal transcriptional signature of three interferon-stimulated genes could predict viral infection in a prospective study. Three Na-VIMs were chosen for measurement: two that encode intracellular proteins (OASL, IFIT2) and the chemokine CXCL10. These three mRNAs are among the most significantly induced by RIG-I ligand in nasal epithelial cells in vitro, as shown in FIG. 1. RNA from 68 nasopharyngeal (NP) swab samples sent to the YNHH clinical laboratory for comprehensive respiratory virus testing was isolated. Samples were collected during 14 designated, and were included in the study if (1) the entire panel of tests for 9 respiratory viruses had been ordered (Table 1), (2) if samples were of sufficient quality for virology testing at YNHH, including direct fluorescent antigen testing as determined by routine microscopy (10.1% of samples eliminated due to quality.) Clinical samples were NP swabs submitted to the clinical laboratory in tubes containing 3 ml viral transport medium (VTM.) Standard respiratory virus PCR testing was performed on nucleic acids isolated from 0.2 ml of viral transport medium and 0.5-1 ml of the remaining VTM was stored at −80° C. and later used for immunoassay. Direct fluorescence antigen (DFA) testing was also performed for a subset of viruses (see Table 1.) For DFA testing, cells were pelleted from the viral transport medium and resuspended in PBS. Remaining cells were again pelleted and resuspended in RLT lysis buffer for RNA isolation for Na-VIM mRNA testing. RT (using iScript reverse transcriptase) and qPCR were performed for 4 transcripts: the housekeeping gene β-actin, and 3 Na-VIMs: OASL, IFIT2, and CXCL10. Patient characteristics are summarized in FIG. 6A-D.

Figures 2A, 2B, 2C:
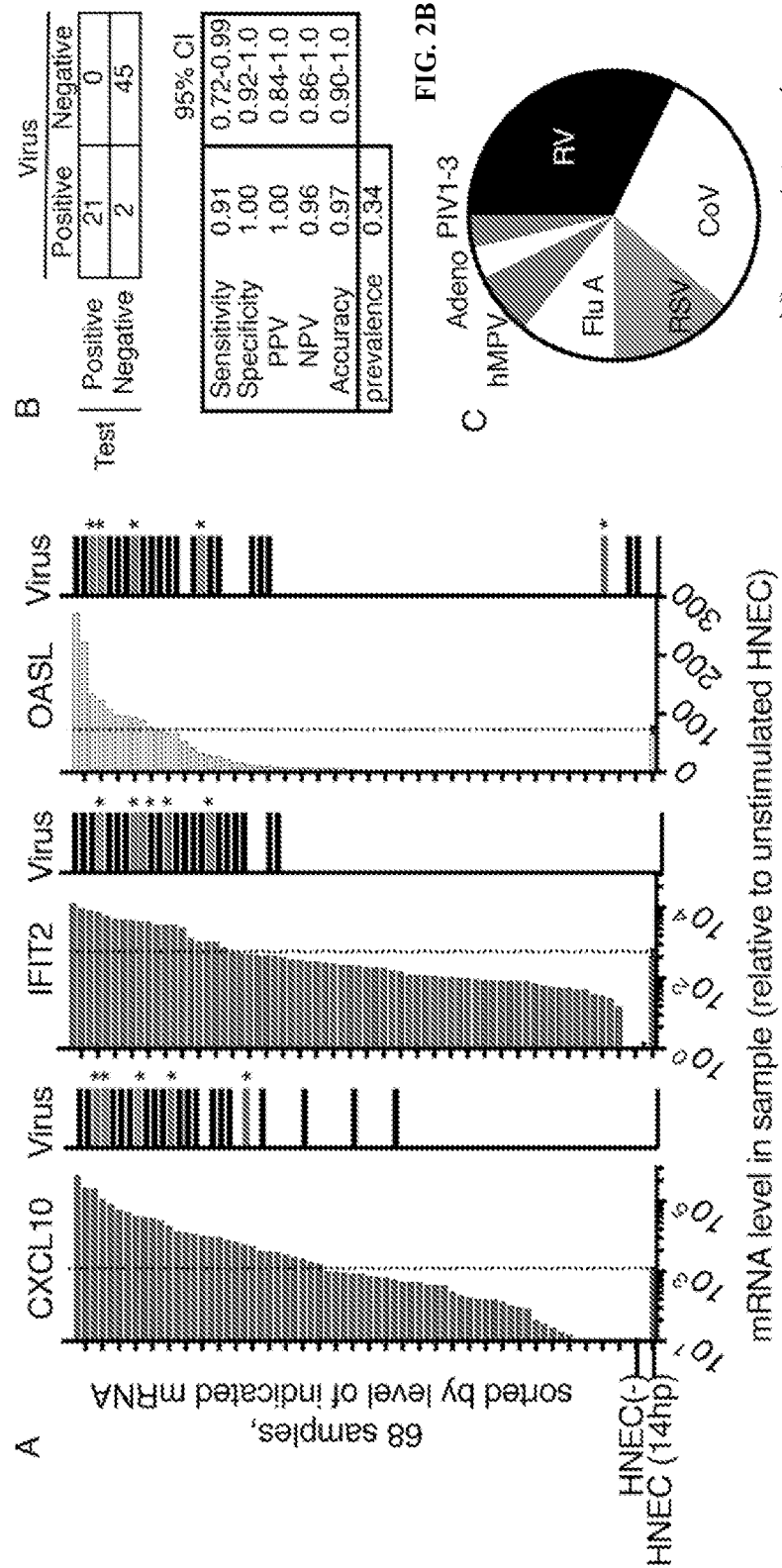
FIGS. 2A-D relate to a RT-qPCR test for three host mRNAs and correlation with respiratory virus detection in 68 in nasopharyngeal swabs (study 1).
Figure 2D:
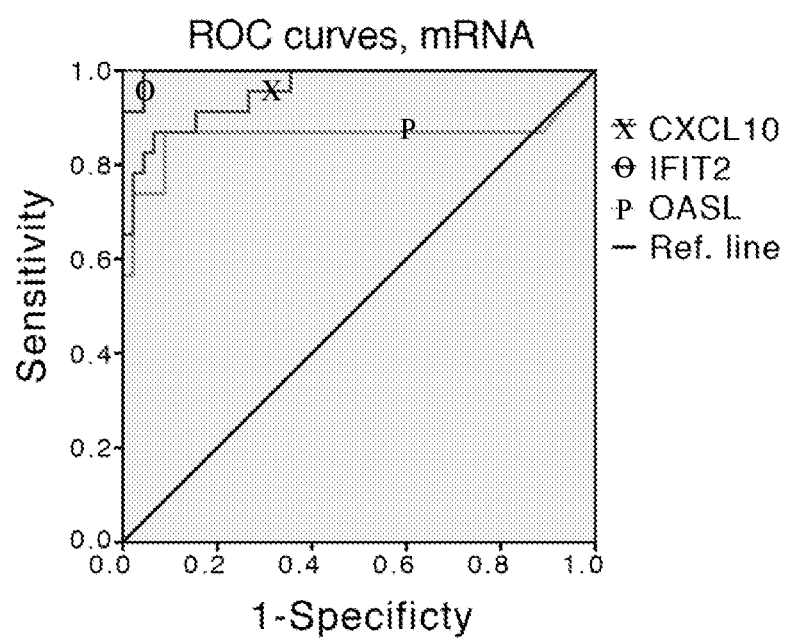

To test the predictive value of Na-VIM mRNA levels, qPCR for these mRNAs was performed and samples were scored by an investigator blinded to the clinical virology and chart review data. The housekeeping gene β-Actin was detectable by RT-qPCR in all samples, however the total amount of RNA obtained per sample was highly variable (<5-300 μg). Therefore Na-VIM transcript levels were normalized to β-actin levels in each sample. To establish empirical cutoffs for each Na-VIM mRNA in the prospective study, qPCR was performed on cultured nasal epithelial cells stimulated with 14 hp in vitro and the Na-VIM mRNA level in stimulated cells was used as the cutoff for scoring an Na-VIM "positive." In each sample, all three Na-VIMs were assessed and the sample was scored as positive for the Na-VIM signature if 2/3 Na-VIM transcript levels exceeded the empirically determined cutoff. Relative mRNA levels for each Na-VIM (bars) and the test result for Na-VIM signature as shown in FIG. 2A.

Comparing the Na-VIM signature results to the standard YNHH testing for a 9-virus respiratory virus panel revealed that all but five samples that scored positive on the Na-VIM signature test also tested positive for known respiratory viruses on YNHH panel. The YNHH virus panel does not include coronaviruses, common respiratory pathogens with RNA genomes. Therefore, qPCR was performed on RNA isolated from all patient samples for 4 coronaviruses (CoV) using a multiplex assay for 4 CoV genotypes. Positive samples were tested with primer sets for individual genotypes. Together these tests revealed that 8/68 specimens were positive for coronavirus OC-43. No other CoV were detected. The viral identity was confirmed with qPCR primers to a different region of the CoV OC-43 genome. Strikingly, all five of the Na-VIM-signature positive samples that would have been called false positives based only on the YNHH virus panel actually contained CoV-0C43. The additional 3 positive samples were detected in samples that had also tested positive for other respiratory viruses (FIG. 2A; samples 1-68 listed chronologically). Using results from the YNHH panel +CoV PCR as the gold standard, the positive predictive value of the 3-Na-VIM signature for the presence of a respiratory virus was 100% (no false positives; 95% C.I. 0.84-1.0 due to sample size.) Of the 68 samples, 2/68 represented false negatives (virus detected in the absence of Na-VIM signature), for a NPV of 0.96 (0.86-1.0), sensitivity of 0.91 (0.72-0.99), and specificity of 1.0 (0.92-1.0). Metrics of test performance are summarized in FIG. 2B. Considering that the YNHH panel did not include coronaviruses, the Na-VIM mRNA signature test was actually more sensitive than the YNHH panel (2/68 false negatives compared to 5/68 false negatives.) Chart review revealed that six of the 68 subjects ultimately tested positive for a respiratory bacterial or fungal pathogen on blood and/or sputum cultures, as indicated by the asterisks on the rightmost panel of FIG. 2A. None of these subjects scored positive on the Na-VIM signature test, suggesting that respiratory infections of non-viral etiology will not lead to a positive test, although a larger study will be needed to test this conclusively.

Example 3: Expression Level of One or Two Na-VIM mRNAs is Sufficient to Rule in Presence of Virus in Many Positive Samples To find the minimum host transcriptional signature needed to "rule in" respiratory virus infection, the diagnostic value of tests based on one or two mRNA biomarkers instead of three was assessed. To visualize the relationship between Na-VIM mRNA levels and the presence of virus, samples were re-ordered from high to low values for each biomarker (FIG. 2A.) These plots reveal that for both CXCL10 and IFIT2 mRNA, high expression always corresponded to virus infection and low expression corresponded to no infection, with an indeterminate zone in between. This was not true for OASL mRNA, although the trend was similar. ROC curve analysis revealed that both IFIT2 and CXCL10 mRNA levels had high diagnostic accuracy for presence of virus (for IFIT2, AUC 0.996, 95% CI 0.99-1.0; for CXCL10, AUC 0.96, 95% C.I. 0.92-1.0; FIG. 2B and Table 3.). Importantly, if the cutoffs were selected to maximize specificity, the IFIT2 level alone could still correctly "rule in" viral infection in 91% (21/23) of specimens and the CXCL10 level alone could "rule in" virus in 70% of samples (15/23). Clinically, setting the threshold to maximize specificity would be useful to create "rule in" tests but not as "rule out" tests due to false negatives.

TABLE 3

ROC curve analysis for mRNA biomarkers

| Test Result Variable(s) | Area | Std. Error[a] | Asymptotic Sig[b] | Asymptotic 95% Confidence Interval | |
|---|---|---|---|---|---|
| | | | | Lower Bound | Upper Bound |
| IFIT2 | .996 | .004 | .000 | .988 | 1.000 |
| OASL | .861 | .066 | .000 | .732 | .991 |
| CXCL10 | .958 | .022 | .000 | .915 | 1.000 |

The test result variable(s): OASL has at least one tie between the positive actual state group and the negative actual state group. Statistics may be biased.
[a]Under the nonparametric assumption
[b]Null hypothesis: true area = 0.5

The performance of an Na-VIM signature combining two biomarkers, IFIT2 and CXCL10, was assessed. Cutoff values determined by ROC analysis were used: for IFIT2, the cutoff was chosen to maximize sensitivity and for CXCL10, a cutoff was chosen to optimize sensitivity and specificity. Samples were scored as positive if both the IFIT2 and CXCL10 values exceeded these cutoffs. Strikingly, test performance was equivalent to testing in the prospective study based on three biomarkers (FIG. 2B) Clinically a test with high diagnostic accuracy could be used as a rule in or rule out test. These analyses reveal the enormous potential of assessing a small number of host biomarkers to identify patients with respiratory virus infection using NP samples.

Example 4: Chemokine Protein Levels in the Viral Transport Medium Correspond to the Presence of Respiratory Virus As indicated in FIG. 1B and Table 2, some of the most highly induced mRNAs triggered by RIG-I ligand in nasal cells in vitro encode secreted proteins, including multiple chemokines. It was investigated whether these proteins could be detected in the transport medium in which the NP swab is placed en route to the clinical laboratory. Aliquots of transport medium that were frozen at the time of collection and stored at −80° C. were used. Even given the relatively large volume of medium (3 ml) and the variability in sample collection, it was possible to detect multiple cytokines in the medium. The study focused on the secreted proteins identified in Table 2. FIG. 3 shows results for 65 samples. Some cytokine levels did not correlate with viral infection; for example CCL20 and IFNL1 (FIGS. 3 and 10.) However, CXCL11, CXCL10, and CXCL9 levels tracked with the presence of virus, analogous to IFIT2 and CXCL10 mRNA levels (FIG. 4.) ROC analysis revealed that CXCL9, 10, and 11 levels have potential predictive value for viral infection.

Area Under the Curve

| Test Result Variable(s) | Area | Std Error[a] | Asymptotic Sig.[b] | Asymptotic 95% Confidence Interval Lower Bound | Upper Bound |
|---|---|---|---|---|---|
| CXCL9 | .870 | .052 | .000 | .767 | .972 |
| CXCL10 | .965 | .019 | .000 | .927 | 1.000 |
| OXCL11 | .971 | .017 | .000 | .937 | 1.000 |

[a]Under the nonparametric assumption
[b]Null hypothesis: true area = 0.5

Figure 4A:
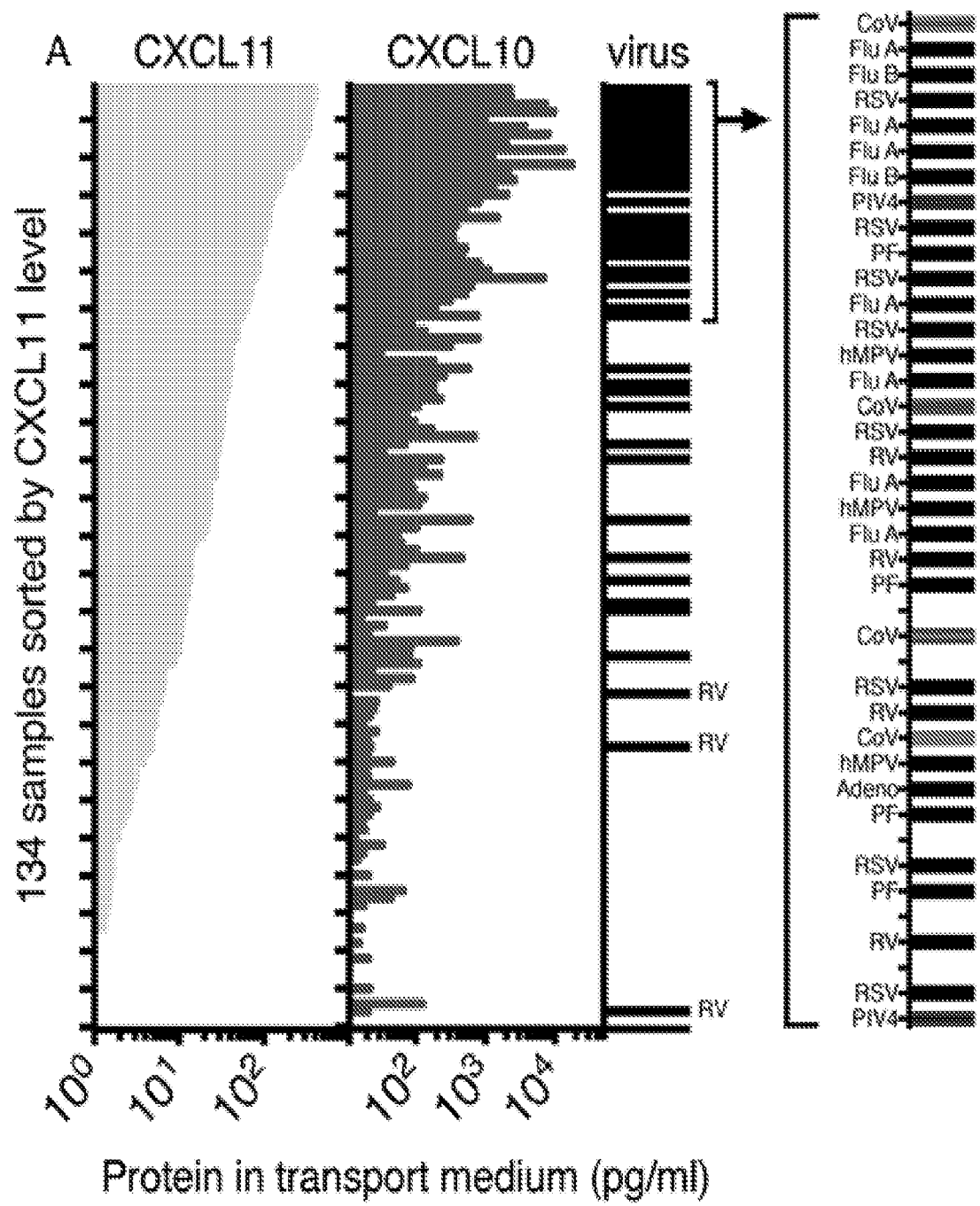
FIGS. 4A-C depict the predictive value of CXCL10 and CXCL11 protein levels for detection of respiratory virus in 134 patient nasopharyngeal swabs. (study #2).
Figure 4B:
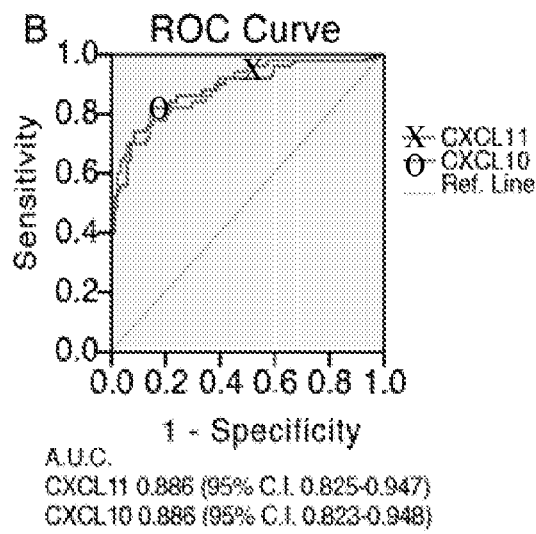
Figure 4C:
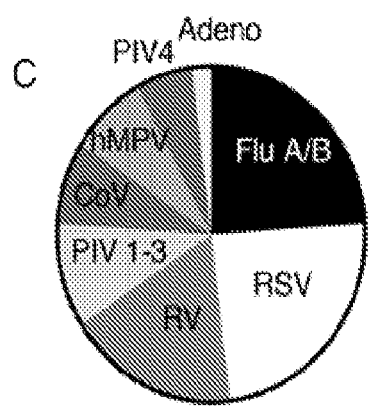

Example 5: CXCL10 and CXCL11 Proteins Each Predict Presence of Respiratory Virus in Second Set of Nasopharyngeal Swabs To further evaluate usefulness of CXCL10 and/or CXCL11 proteins in predicting respiratory virus infection, levels of both proteins were measured in viral transport medium in a second set of 134 stored samples sent to the hospital virology lab for testing. Samples were selected using the same criteria as in study 1, except that the analysis was limited to samples from patients >2 years old due to concerns about effects of differences in sample size and collection from children under 2 years old. Levels of both CXCL10 and CXCL11 correlated highly with the presence of viral infection as detected using the 13-virus panel (9-virus YNHH panel plus the 4-coronavirus panel used in study 1; FIG. 4A.) However, several virus-negative samples associated with very high levels of CXCL10 or CXCL11. To determine whether these were false positives and true positives (biomarker positive samples that were also positive for untested viruses), the test panel was further expanded by testing for parainfluenza virus type 4. Three samples were positive for PIV4, including one co-detection and two samples negative for other viruses on the panel, but with high CXCL10 and CXCL11 levels. FIG. 4A shows the correlation between CXCL10 and CXCL11 concentrations in the transport medium and virus detection. The viruses detected in the 40 samples with the highest [CXCL11] are indicated, with shaded bars in the "virus" panel indicating samples that were positive for virus only after testing with the CoV panel or the PIV4 test. As shown, there were also chemokine-high samples with no virus detected, and chemokine-low samples with viruses detected (FIG. 4A.) Rhinovirus was the virus detected in the three virus positive samples with the lowest chemokine levels. Altogether, however, the second sample set also showed a high correlation of levels of both CXCL10 and CXCL11 with virus detection. Using the virology data from the expanded panel as the gold standard, the overall correlation between each of these protein levels and presence of viral infection was high and comparable for each biomarker (CXCL11; AUC=0.886, 95% CI 0.825-0.947; CXCL10, AUC 0.886 95% CI 0.823-0.948; FIG. 4B). Overall, 50/134 of samples (36%) were positive for ten distinct viruses including influenza A and B and CoV-0C43 and 229E (FIG. 4C.)

To visualize the possible tests that could be developed using CXCL10 or CXCL11 as biomarkers of viral infection in this sample type, [CXCL11] was plotted in all 202 samples, sorted from highest to lowest concentration. A consistent pattern in both studies is that high chemokine level correlated strongly with virus detection and low levels correlated with absence of virus, with intermediate levels being indeterminate. Based on this pattern, it is possible to envision developing a rule-in/rule-out test using a high cutoff above which samples are predicted to be virus positive, and below which samples are predicted to be virus-negative. Dashed grey lines represent a cutoff of >80 pg/ml for rule-in, which in this sample set would have a positive predictive value of 90%; dotted black lines indicate a low cutoff of 8.5 pg/ml, below which this test has a negative predictive value of 96%. Using these cutoffs, about 1/3 of the samples (37%) fall into the intermediate indeterminate zone. Notably, there is a high correlation between levels of CXCL10 and CXCL11 in these samples (FIG. 4B; $R^2$=0.80) A similar test could be made using CXCL10 instead of CXCL11, as the AUC for both indicates high potential for usefulness as biomarkers of viral infection (in set of 200 samples, CXCL11 AUC=0.905; 95% CI 0.86-0.95; CXCL10 AUC=0.88; FIG. 4B.) In sum, these results demonstrate that an immunoassay based test measuring a single host protein could have high diagnostic utility for managing patients with suspected respiratory infection.

A subset of host mRNAs and proteins associated with the antiviral interferon response are readily detectable in nasopharyngeal swab samples and correlate with viral infection. In this study, it was tested whether mRNAs and proteins associated with NP swabs could be used to predict the detection of a respiratory virus. In both nasal epithelial cells following RIG-I stimulation in vitro and NP swabs containing respiratory viruses, enriched mRNAs and proteins included many molecules known to be induced during the antiviral interferon response, a key host defense pathway in which viral recognition leads to interferon secretion and induction of ~300 different antiviral effectors. While this result is not unexpected, it is important to note that interferon-stimulated genes have diverse regulatory mechanisms, are differentially expressed in different host tissues, and are differentially antagonized by different viruses. Therefore, identifying which one(s) perform best as pan-viral infection biomarkers in the upper respiratory tract requires empirical testing.

Interestingly, although induction of many different chemokines by RIG-I stimulation was observed in vitro, only one family of chemokines correlated highly with viral infection in NP swab samples: the CXCR3 ligands CXCL9, CXCL10, and CXCL11. These ligands mediate chemotaxis of T cells to the site of viral infection. The consistent detection of high levels of these chemokines but not others in nasopharyngeal samples from patients with diverse respiratory viruses suggests a particularly robust and conserved role for these chemokines in local antiviral defense of the upper respiratory tract.

These examples show that it is possible to define an mRNA signature with very high diagnostic accuracy for predicting virus infection by comparing the level of mRNA biomarkers in patient samples to levels in resting cultured nasal epithelial cells and combining the information from three biomarkers (FIG. 3 accuracy of 97% (95% C.I.90-100%); sensitivity 91%; specificity 100%) This test compared favorably with an mRNA based index correlating Viperin mRNA levels to viral infection in this sample type (sensitivity of 80%, specificity 94%). Is it possible to develop a practical diagnostic test that employs mRNA isolation and RT-qPCR for several targets? Technologies to support such tests in the clinical lab and at point of care are under active development. While mRNA-based signatures may not soon become point of care technologies, such tests could be performed by a central lab, for example as part of the work-up for a complex patient to determine whether respiratory virus infection is part of the disease process and merits more extensive diagnostic testing.

Figure 5:
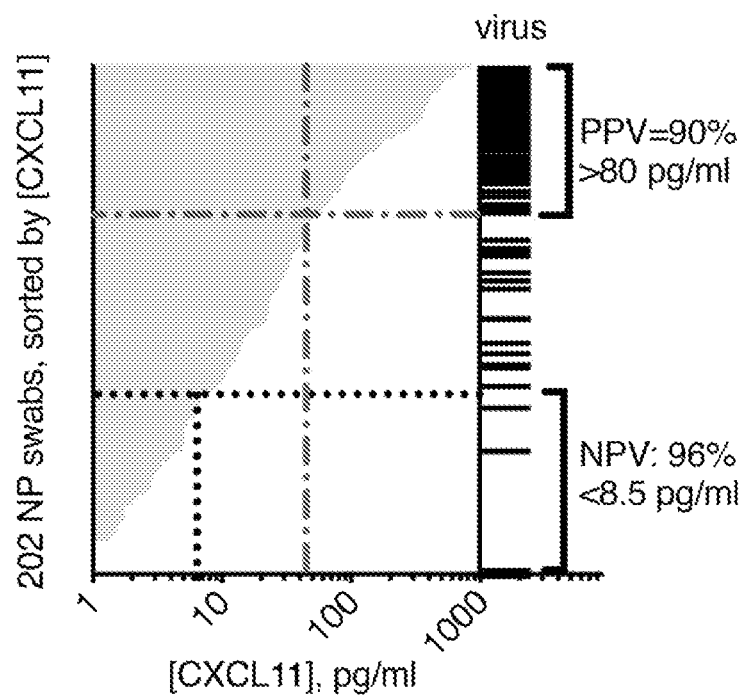
FIG. 5 illustrates a possible rule in/rule out test for viral respiratory infection based on CXCL11 protein level, using data from 202 nasopharyngeal swabs (study 1+study 2). Demonstration of how CXCL11 level could be used to create a rule-in/rule-out test for respiratory virus infection. Plot shows CXCL11 concentrations measured in 202 samples (study 1+study 2), sorted by CXCL1 level. Black bars represent presence of virus. Brackets show how cutoffs could be used to rule in or rule out viral infection at the upper and lower ends of [CXCL11], with an intermediate indeterminate zone in this patient population (prevalence of virus detection=36%.). Brackets demonstrate that for ~2/3 of the samples (63%), virus infection can be ruled in with a positive predictive value of 90% and ruled out with a negative predictive value of 96%; for 1/3 of samples, test is indeterminate.
Figure 6A:
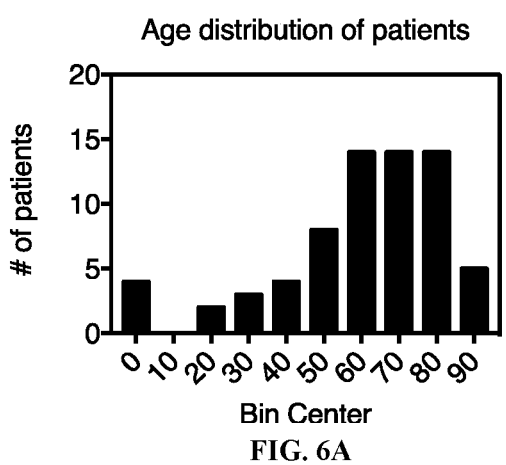
FIGS. 6A-D depict patient characteristics for the mRNA biomarker study of 68 nasopharyngeal swabs (study 1).
Figure 6B:
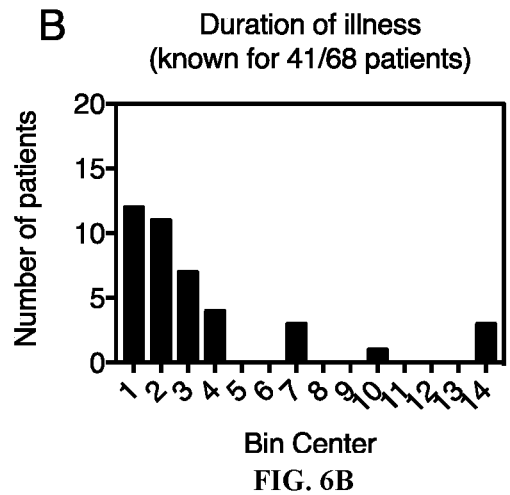
Figure 6C:
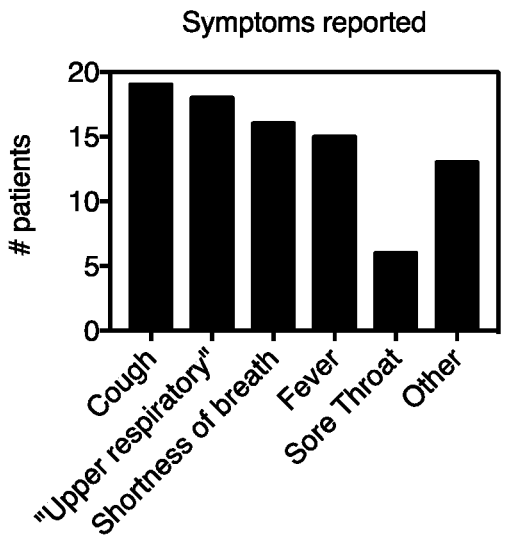
Figure 6D:
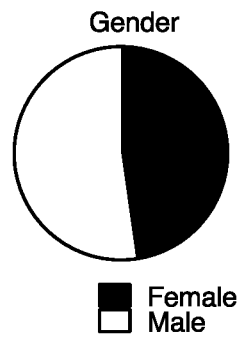
Figure 7:
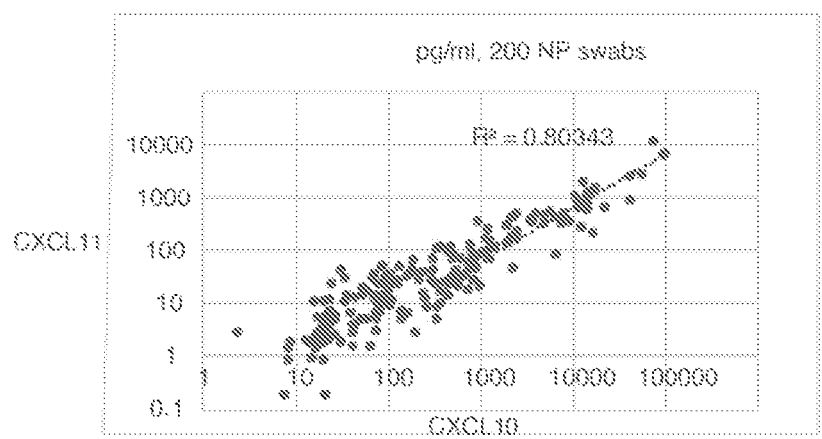
FIG. 7 depicts the correlation between [CXCL11] and [CXCL10], in 202 NP swabs.

Usefulness of protein biomarkers to rule in viral infection. These findings indicate that CXCL10 or CXCL11 protein levels in NP swab transport medium could serve as useful biomarkers to rule in viral infection when the cause of respiratory symptoms is unclear. With a few exceptions, high levels of these proteins identified virus-positive samples and low levels identified virus-negative samples with an intermediate, indeterminate zone. This means that a cutoff could be chosen to optimize positive predictive value. For example, using a cutoff of CXCL11 levels above 80 pg/ml lead to a PPV of 90% (FIG. 5); using a cutoff of CXCL11 levels above 215 pg/ml lead to a PPV of 97%. A robust, cost-effective rule-in a test would be extremely useful for guiding the workup of hospitalized patients. Furthermore, immunoassay based tests are easily adapted to point-of-care use and a test to rule in viral infection could be tremendously useful for outpatient management if the biomarkers described here also perform well in the outpatient population.

Figure 8:
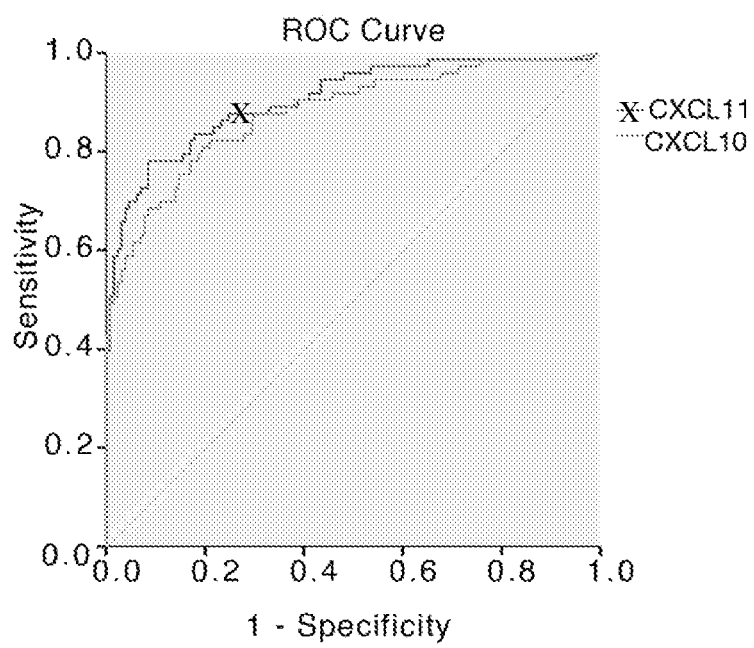
FIG. 8 depicts ROC curves showing correlation between [CXCL11] or [CXCL10] (pg/ml) in NP swab transport medium and detection of respiratory virus in 202 NP swabs (study 1+study 2.) Relationship between chemokine protein level and presence of virus was calculated using SPSS statistics.

Preliminary analysis indicates that low CXCL10 or CXCL11 levels could serve as a robust rule-out test (FIG. 8.) However, biomarker negative, virus positive samples were observed. There are many possible explanations, including the possibility that some virus strains block or fail to induce robust chemokine responses. Alternatively, low biomarker levels could be associated with incidental detections or resolved infections that are not currently part of an active disease process. Interestingly, in both studies, virus-positive samples with the lowest levels of CXCL11 and CXCL10 contained rhinovirus. In community surveys, this virus is more highly associated with incidental detections than other viruses, with almost half of detections asymptomatic in one family survey. Emerging evidence suggests that host antiviral responses can be detected at the mRNA level in the respiratory tract of asymptomatic virus-infected subjects, but that the magnitude of transcriptional antiviral response (and possibly the presence of a response at the protein level) is greater in symptomatic than asymptomatic subjects.

Additional uses for a simple host response-based test for respiratory virus infection. Host-response based testing could be used to improve the efficiency of diagnosing respiratory illness, and offers a cost-effective alternative to testing for large panels of viruses, and/or provide a way of "triaging" which samples should receive further testing with more costly testing for panels of multiple respiratory viruses. In addition, this type of testing may have other uses. For example, for some viruses, such as emerging respiratory pathogens, there are no virus-specific tests available. In fact, in the case of an emerging respiratory syndrome, even the type of disease process (e.g., bacterial infection vs. viral infection vs. toxin) may be unknown. In this setting, a general test detecting that the patient's respiratory tract is responding to a viral infection would fill an unmet need. The usefulness of the host response test in identifying an unexpected virus was illustrated by this study, in which host response tests identified samples positive for viruses that were not on the original 9-virus test panel (see colored bars in virus column, FIGS. 2 and 4).

In sum, these result show that biomarkers of the antiviral response are robustly detected using nasopharyngeal swabs, including protein biomarkers detected with an immunoassay, and that even single protein biomarkers detected using this minimally-invasive sample type have high diagnostic accuracy. These results compel further study using nasopharyngeal biomarkers for improving the understanding of host/virus interactions, and for improving the diagnosis and management of patients with respiratory illness.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for detecting a respiratory virus in a patient, the method comprising:
   a. analyzing a viral transport medium sample to determine a level of at least one nasal virus-induced molecule and a level of a housekeeping gene by measuring mRNA;
   b. normalizing the level of the at least one nasal virus-induced molecule to the level of the housekeeping gene to determine a normalized level of the at least one nasal virus-induced molecule; and
   c. comparing the normalized level of the at least one nasal virus-induced molecule with a predetermined reference level for the at least one nasal virus-induced molecule;
   wherein the method further comprises determining the level of interferon lambda 1 (IFNL1) as an indicator of sample quality; and
   wherein if the normalized level of the at least one nasal virus-induced molecule is above the respective reference level, the patient is determined to have a respiratory viral infection.

2. The method of claim 1 wherein the mRNA is measured by reverse transcription-qPCR.

3. The method of claim 1, wherein the at least one nasal virus-induced molecule is interferon-induced protein with tetratricopeptide repeats (IFIT) 1 (IFIT1), IFIT2, IFIT3, 2'-5' oligoadenylate synthetase-like (OASL), 2'-5' oligoadenylate synthetase (OAS) 1 (OAS1), OAS2, OAS3, interferon-stimulated gene 15 (ISG15), interferon induced with helicase C domain 1 (IFIH1), interferon induced protein 44 (IFI44), DExD/H-box helicase (DDX) 58 (DDX58), DDX60, DDX60-like (DDX60L), HECT and RLD domain containing E3 ubiquitin protein ligase 5 (HERC5), myxovirus resistance (MX) 1 (MX1), MX2, interferon induced transmembrane protein 1 (IFITM1), radical S-adenosyl methionine domain containing 2 (RSAD2), IFI44-like (IFI44L), interferon alpha inducible protein 27 (IFI27), DExH-box helicase 58 (DHX58), C—X—C motif chemokine ligand (CXCL) 10 (CXCL10), C—X3-C motif chemokine ligand 1 (CX3CL1), CXCL8, CXCL11, CXCL1, interleukin 36 gamma (IL36G), CXCL9, interferon lambda 2 (IFNL2), CXCL2, tumor necrosis factor (TNF), CXCL3, or C—C motif chemokine ligand 22 (CCL22).

4. The method of claim 1 wherein the housekeeping gene comprises β-actin, hypoxanthine phosphoribosyltransferase (HPRT), or glyceraldehyde β-phosphate dehydrogenase (GAPDH).

5. A method for detecting a respiratory virus in a patient, the method comprising:
   a. analyzing a viral transport medium sample to determine a level of at least one nasal virus-induced molecule by measuring protein; and
   b. comparing the level of the at least one nasal virus-induced molecule with a predetermined reference level for the at least one nasal virus-induced molecule;
   wherein the method further comprises determining the level of interferon lambda 1 (IFNL1) as an indicator of sample quality; and
   wherein if the level of the at least one nasal virus-induced molecule is above the respective reference level, the patient is determined to have a respiratory viral infection.

6. The method of claim 5 wherein the level of the protein encoded by nasal virus-induced molecule is measured by immunoassay.

7. The method of claim 5 wherein the protein is an interferon or a chemokine.

8. The method of claim 5, wherein the at least one nasal virus-induced molecule is interferon-induced protein with tetratricopeptide repeats (IFIT) 1 (IFIT1), IFIT2, IFIT3, 2'-5' oligoadenylate synthetase-like (OASL), 2'-5' oligoadenylate synthetase (OAS) 1 (OAS1), OAS2, OAS3, interferon-stimulated gene 15 (ISG15), interferon induced with helicase C domain 1 (IFIH1), interferon induced protein 44 (IFI44), DExD/H-box helicase (DDX) 58 (DDX58), DDX60, DDX60-like (DDX60L), HECT and RLD domain containing E3 ubiquitin protein ligase 5 (HERC5), myxovirus resistance (MX) 1 (MX1), MX2, interferon induced transmembrane protein 1 (IFITM1), radical S-adenosyl methionine domain containing 2 (RSAD2), IFI44-like (IFI44L), interferon alpha inducible protein 27 (IFI27), DExH-box helicase 58 (DHX58), C—X—C motif chemokine ligand (CXCL) 10 (CXCL10), C—X3-C motif chemokine ligand 1 (CX3CL1), CXCL8, CXCL11, CXCL1, interleukin 36 gamma (IL36G), CXCL9, interferon lambda 2 (IFNL2), CXCL2, tumor necrosis factor (TNF), CXCL3, or C—C motif chemokine ligand 22 (CCL22).

9. The method of claim 1 wherein the levels of at least two nasal virus-induced molecules are determined, normalized and compared to the respective reference levels of the nasal virus-induced molecules.

10. The method of claim 1 wherein the level of at least three nasal virus-induced molecules are determined, normalized and compared to the respective reference levels of the nasal virus-induced molecules.

11. A method of determining whether a respiratory virus is involved in an active disease process compared with incidental detection, the method comprising:

a. analyzing a viral transport medium sample from the patient to determine a level of at least one nasal virus-induced molecule and a level of a housekeeping gene;

b. normalizing the level of the at least one nasal virus-induced molecule to the level of the housekeeping gene to determine a normalized level of the at least one nasal virus-induced molecule; and c. comparing the normalized level of the at least one nasal virus-induced molecule with a predetermined reference level for the at least one nasal virus-induced molecule;

wherein the method further comprises determining the level of interferon lambda 1 (IFNL1) as an indicator of sample quality; and wherein if the normalized level of the at least one nasal virus-induced molecule is above the reference level, the respiratory virus is determined to be in the active disease process.

12. A method for detecting a respiratory virus in a patient, the method comprising:

a. analyzing a viral transport medium sample to determine a level of at least one nasal virus-induced molecule by measuring protein; and b. comparing the level of the at least one nasal virus-induced molecule with a predetermined reference level for the at least one nasal virus-induced molecule; and, wherein the method further comprises determining the level of interferon lambda 1 (IFNL1) as an indicator of sample quality; and wherein if the level of the at least one nasal virus-induced molecule is below the respective reference level, the patient is determined not to have a respiratory viral infection.

\* \* \* \* \*

SEQUENCE LISTING

<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: Primer

<400> SEQUENCE: 1
cctggcaccc agcacaat                                                 18

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
gccgatccac acggagtact                                               20

```
<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
aaggtagtca aggtgggctc                                               20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
ctcctggaag ctgtggaaac                                               20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
cctcaaaggg caaaacgagg                                               20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ctgatttctg cctggtcagc                                               20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
cctgcaagcc aattttgtcc                                               20

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
atggccttcg attctggatt c                                             21

<210> SEQ ID NO 9
<211> LENGTH: 23
<212> TYPE: DNA
<213> ORGANISM: Artificial Sequence
<220> FEATURE:
<223> OTHER INFORMATION: Primer
```

-continued

```
<400> SEQUENCE: 9
cgatgaggct attccgacta ggt                                              23

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
ccttcctgag ccttcaatat agtaacc                                          27

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gagcttgaag gtgtaggtgc                                                  20

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
caagaacttc ctcgccagc                                                   19
```